US009469635B2

(12) United States Patent
Sudhakar et al.

(10) Patent No.: US 9,469,635 B2
(45) Date of Patent: *Oct. 18, 2016

(54) STABLE SNS-595 COMPOSITIONS AND METHODS OF PREPARATION

(71) Applicant: SUNESIS PHARMACEUTICALS, INC., South San Francisco, CA (US)

(72) Inventors: Anantha Sudhakar, Fremont, CA (US); Jeff Jacobs, San Mateo, CA (US); Ahmad Hashash, Pleasant Hill, CA (US); Sean Ritchie, Fremont, CA (US); Hengqin Cheng, Foster City, CA (US)

(73) Assignee: Sunesis Pharmaceuticals, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/055,590

(22) Filed: Oct. 16, 2013

(65) Prior Publication Data
US 2014/0275547 A1 Sep. 18, 2014

Related U.S. Application Data

(63) Continuation of application No. 12/875,927, filed on Sep. 3, 2010, now Pat. No. 8,586,601.

(60) Provisional application No. 61/240,161, filed on Sep. 4, 2009.

(51) Int. Cl.
A61K 31/4375 (2006.01)
C07D 471/04 (2006.01)
C07D 417/14 (2006.01)
C07D 417/04 (2006.01)

(52) U.S. Cl.
CPC ........... C07D 471/04 (2013.01); C07D 417/04 (2013.01); C07D 417/14 (2013.01)

(58) Field of Classification Search
CPC ............ A61K 31/4375; C07D 471/04; C07D 417/14
See application file for complete search history.

(56) References Cited

U.S. PATENT DOCUMENTS

| 5,817,669 | A | 10/1998 | Tomita et al. |
| 7,829,577 | B2 | 11/2010 | Nakao et al. |
| 7,968,565 | B2 | 6/2011 | Arkin et al. |
| 7,989,468 | B2 | 8/2011 | Adelman et al. |
| 8,124,773 | B2 | 2/2012 | Adelman et al. |
| 8,138,202 | B2 | 3/2012 | Sudhakar et al. |
| 8,470,817 | B2 | 6/2013 | Sudhakar et al. |
| 8,497,282 | B2 | 7/2013 | Sudhakar et al. |
| 8,518,872 | B2 | 8/2013 | Silverman |
| 2006/0025437 | A1 | 2/2006 | Adelman et al. |
| 2006/0063795 | A1 | 3/2006 | Arkin et al. |
| 2008/0063642 | A1 | 3/2008 | Adelman et al. |
| 2009/0263393 | A1 | 10/2009 | Adelman et al. |
| 2010/0048609 | A1 | 2/2010 | Jacobs |
| 2011/0008371 | A1 | 1/2011 | Michelson et al. |
| 2011/0082169 | A1 | 4/2011 | Sudhakar et al. |
| 2011/0105497 | A1 | 5/2011 | Sudhakar |
| 2011/0263524 | A1 | 10/2011 | Arkin et al. |
| 2011/0312988 | A1 | 12/2011 | Higaki et al. |
| 2012/0148564 | A1 | 6/2012 | Hawtin et al. |
| 2012/0245198 | A1 | 9/2012 | Adelman et al. |
| 2013/0102559 | A1 | 4/2013 | Michelson et al. |
| 2013/0244967 | A1 | 9/2013 | Arkin et al. |

FOREIGN PATENT DOCUMENTS

| JP | 11-349565 | 6/1998 |
| JP | 2003/127542 | 5/2003 |

OTHER PUBLICATIONS

Kumar et al., *Tet. Lett.*, 2003, 5687-5689, vol. 44.
Tsuzuki, et al., *Bio. & Med. Chem.*, 2004, 3189-3193, vol. 14.
Tsuzuki, et al., *J Med. Chem.*, 2004, 2097-2106, vol. 47.
Tomita, et al., *J. Med. Chem.*, 2002, 5564-5575, vol. 45.
Tsuzuki et al., *Tet. Asym.*, 2001, 2989-2997, vol. 12.
Tsuzuki et al., *Tet. Asym.*, 2001,1793-1799, vol. 12.

*Primary Examiner* — Sahar Javanmard
(74) *Attorney, Agent, or Firm* — Jones Day

(57) ABSTRACT

Methods of preparing substantially pure SNS-595 substance are disclosed. Also provided are compositions comprising SNS-595 substance that are substantially pure and essentially free of visible particles.

16 Claims, 3 Drawing Sheets

FIG. 1

STABLE SNS-595 COMPOSITIONS AND METHODS OF PREPARATION

This application claims priority under 35 U.S.C. §120 to, and is a continuation of, U.S. application Ser. No. 12/875,927, filed Sep. 3, 2010, which claims the benefit under 35 U.S.C. §119(e) of U.S. Provisional Application No. 61/240,161, filed Sep. 4, 2009, the entireties of each of which is are incorporated herein by reference.

1. FIELD

Methods are provided for preparing substantially pure (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid, together with compositions comprising this substance.

2. BACKGROUND

The compound (+)-1,4-dihydro-7-[(3S,4S)-3-methoxy-4-methylamino-1-pyrrolidinyl]-4-oxo-1-(2-thiazolyl)-1,8-naphthyridine-3-carboxylic acid, has the following chemical structure:

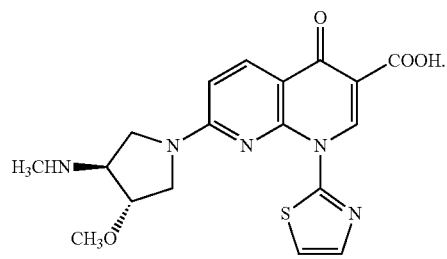

This compound is also known as SNS-595 or AG-7352. The United States Adopted Names Council (USANC) has assigned the name "vosaroxin" to this compound.

SNS-595 is known for its anti-tumor activity (see, Tsuzuki et al., *J. Med. Chem.*, 47:2097-2106, 2004 and Tomita et al., *J. Med. Chem.*, 45:5564-5575, 2002). Treatment of various cancers with SNS-595 has been proposed in the literature, and SNS-595 has shown preclinical activity against various cancer cell lines and xenografts. Various dosing regimens for the use of this compound have been reported. For example, see U.S. Patent Application Pub. Nos. 2005-0203120 A1, 2005-0215583 A1, and 2006-0025437 A1, all of which are incorporated herein by reference in their entireties. SNS-595 is presently being tested in clinical trials to assess safety and efficacy in human cancer patients, and has demonstrated clinical activity in the treatment of acute myeloid leukemia and ovarian cancer.

SNS-595 can be prepared using techniques known to those of ordinary skill in the art. See, for example, U.S. Pat. No. 5,817,669, issued Oct. 6, 1998; Japanese Patent Application No. Hei 10-173986, published Jun. 26, 1998; WO 2007/146335, published Dec. 21, 2007; Tsuzuki et al., *J. Med. Chem.*, 47:2097-2106, 2004; and Tomita et al., *J. Med. Chem.*, 45:5564-5575, 2002, all of which are incorporated herein by reference in their entireties.

International Patent Application No. WO 2007/146335 describes an exemplary process for the synthesis of SNS-595. As shown in Scheme 1, this synthesis proceeds via Intermediate 1, which is reacted with Compound 2 in the presence of a base, such as triethylamine or N,N-diisopropylethylamine to form Compound 3. The ester group of Compound 3 is subsequently hydrolyzed to afford SNS-595.

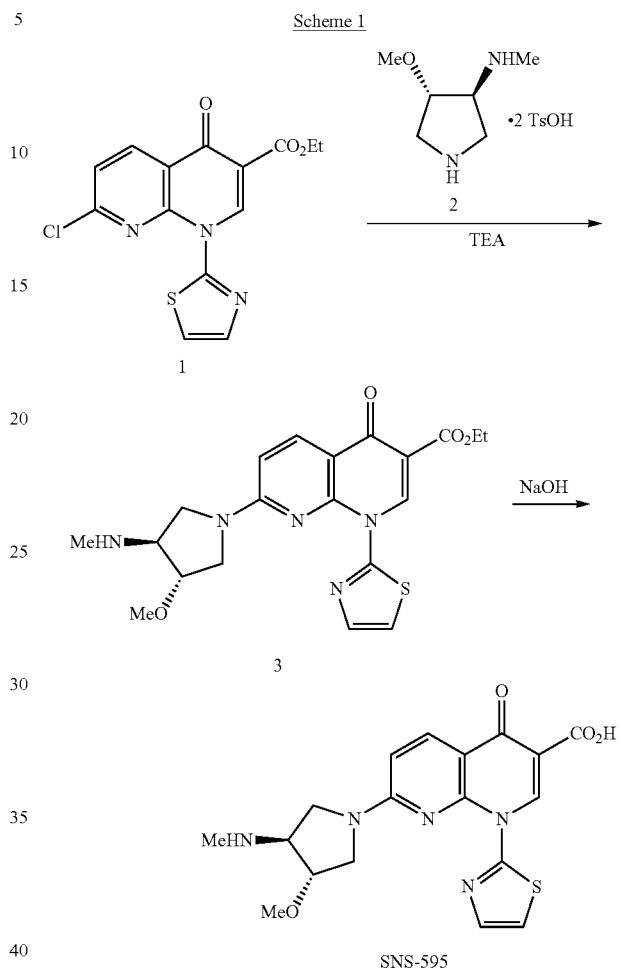

The route described in Scheme 1, however, typically yields undesirable amounts of impurities, i.e., by-products of the reactions, which are difficult to deplete or remove from the SNS-595 drug substance and SNS-595 drug products.

Although certain by-products can exist in SNS-595 preparations, reducing the amount of these impurities in the drug substance and the final drug product is important. Since cancer patients undergo significant chemotherapy and radiation therapy and can, therefore, have compromised immune systems, it is beneficial to deliver to these patients drug product that is characterized by high purity. Further, for intravenous or intraarterial administration of a drug product, the purity and physical characteristics of the drug product are important because the drug product enters directly into the bloodstream.

Thus, there remains a need for improved methods for preparing SNS-595 substantially free of contaminants, thereby providing a drug substance in a substantially pure form that is well suited for formulation into pharmaceutical products for the treatment of cancer without the need for laborious purification steps.

3. SUMMARY

Processes are provided that can yield a substantially pure SNS-595 substance. In addition, the processes can be scaled up to commercial manufacturing of substantially pure SNS-595 substance.

In some embodiments, processes are provided for preparing a substantially pure SNS-595 substance, comprising:
(a) reacting Compound 3

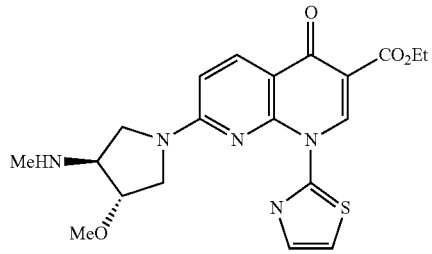

with a first aqueous base followed by neutralizing to obtain a primary SNS-595 hydrate;
(b) dehydrating the primary SNS-595 hydrate from step (a) and reacting the dehydrated product with a second aqueous base followed by neutralizing to obtain a secondary SNS-595 hydrate; and
(c) dehydrating the secondary SNS-595 hydrate obtained in step (c) to obtain the substantially pure SNS-595 substance.

In some cases, it may be desirable to react the substantially pure SNS-595 substance obtained in step (c) with a further aqueous base, neutralize, and then dehydrate to further improve the purity of the substantially pure SNS-595 product. The first aqueous base, the second aqueous base, and the further aqueous base(s) can be the same or different. Likewise, the acids employed during the neutralization steps may be the same or different. Recycling of the substantially pure SNS-595 substance through the described steps of treatment with aqueous base, neutralization, and dehydration may be performed a plurality of times to sequentially further purify the SNS-595 substance until a substantially pure SNS-595 substance of a desired level of purity is obtained.

In some embodiments, processes are provided for preparing a substantially pure SNS-595 substance, comprising:
(a) reacting Compound 1

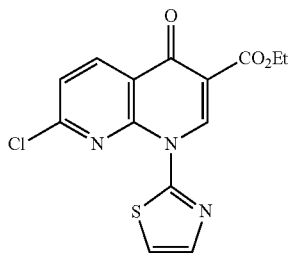

with Compound 2

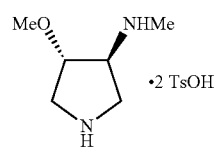

in the presence of N,N-diisopropylethylamine and water to obtain substantially pure

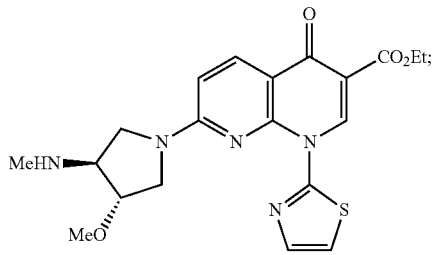

and
(b) reacting Compound 3 with an aqueous base to form the substantially pure SNS-595 substance.

In some embodiments, provided herein are compositions comprising substantially pure SNS-595 substance, wherein the substantially pure SNS-595 substance comprises about 0 to 0.01% Compound 4

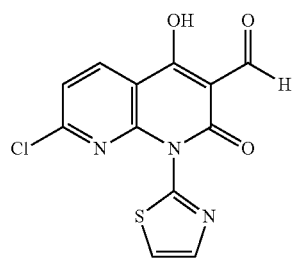

at the time of production of the compositions, based on total weight of the substantially pure SNS-595 substance.

In some embodiments, provided herein are compositions comprising substantially pure SNS-595 substance, wherein the substantially pure SNS-595 substance comprises about 0 to 0.02% Compound 5

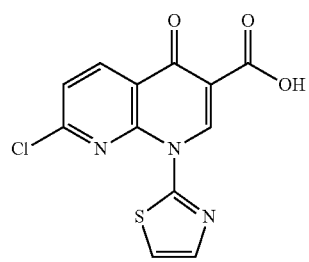

at the time of production of the compositions based on total weight of the substantially pure SNS-595 substance.

In some embodiments, compositions are provided that comprise SNS-595 and water, wherein about 100 mg of SNS-595 is present for every 10 mL of the compositions, wherein the compositions are essentially free of visible particles, and wherein the compositions are stable at, for example, 3, 6, 9, 12, or 24 months after production.

In some embodiments, compositions are provided that comprise SNS-595 and water, wherein about 100 mg of SNS-595 is present for every 10 mL of the compositions, wherein the compositions are essentially free of sub-visible particles, and wherein the compositions are stable at, for example, 3, 6, 9, 12, or 24 months after production.

In some embodiments, the processes described herein are performed on a kilogram scale.

4. BRIEF DESCRIPTION OF THE DRAWINGS

FIG. 1 illustrates the observed relationship between amounts of Compound 6 in SNS-595 bulk drug product solutions formulated from drug substances having different amounts of Compound 4.

5. DETAILED DESCRIPTION

4.1 Definitions

Figure 2:
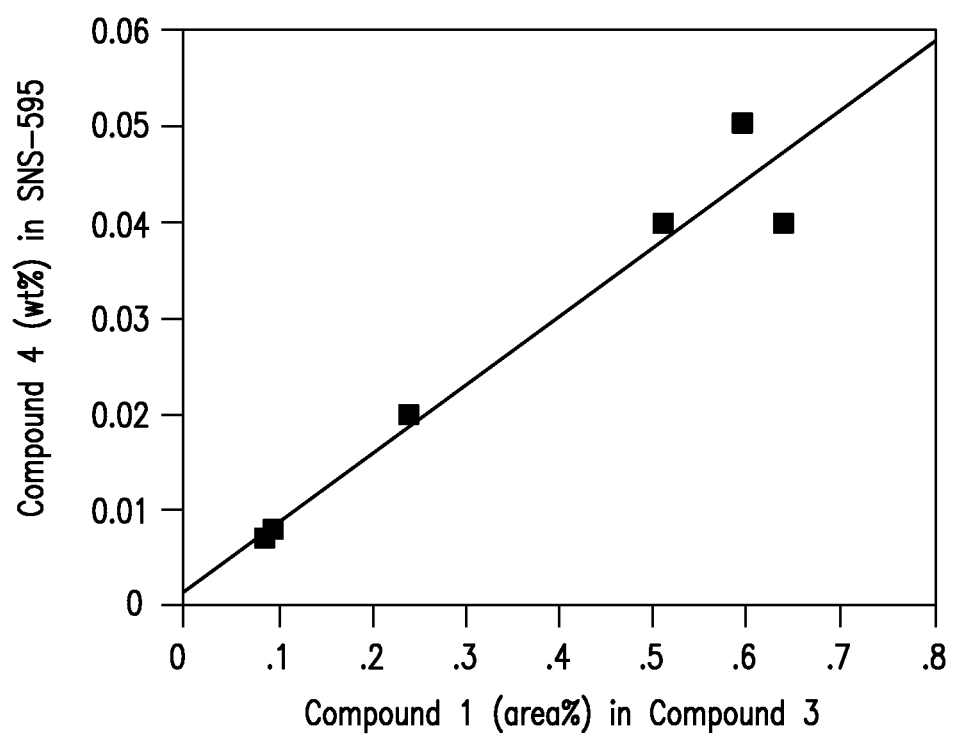
FIG. 2 illustrates the observed relationship between the amount of Compound 4 in SNS-595 drug substance and the amount of residual Compound 1 in Compound 3 used to prepare the drug substance.

Unless defined otherwise, all technical and scientific terms used herein have the same meaning as is commonly understood by one of ordinary skill in the art. All patents, applications, published applications and other publications mentioned herein are incorporated by reference in their entirety.

As used herein, "SNS-595" refers to (+)-1,4-dihydro-7-[(3S,4S)-3-methoxy-4-methylamino-1-pyrrolidinyl]-4-oxo-1-(2-thiazolyl)-1,8-naphthyridine-3-carboxylic acid, as well as any ionic form, salts, solvates, e.g., hydrates, or other forms of that compound, including mixtures thereof. Thus, compositions comprising SNS-595 include (+)-1,4-dihydro-7-[(3S,4S)-3-methoxy-4-methylamino-1-pyrrolidinyl]-4-oxo-1-(2-thiazolyl)-1,8-naphthyridine-3-carboxylic acid or, in some embodiments, an ionic form thereof, salt, solvate, e.g., hydrate, polymorph, pseudomorph, or other form of the compound. In some embodiments, SNS-595 is provided as a pharmaceutically acceptable salt. SNS-595 is also referred to as AG-7352, voreloxin, and vosaroxin.

As used herein, "substantially pure SNS-595 substance" refers to a composition consisting essentially of SNS-595, i.e., comprising less than about 1.0% of any other individual compound or impurity based on total weight of the composition (wt %). For example, in some embodiments, such compositions comprise about 0 to 0.5%, about 0 to 0.1%, about 0 to 0.05%, about 0 to 0.03%, about 0 to 0.02%, or about 0 to 0.01% Compound 4 based on total weight of the composition.

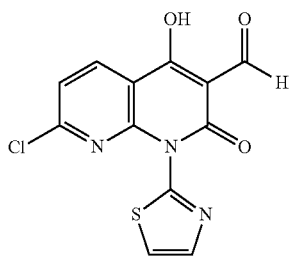

In some embodiments, such compositions consist essentially of 0 to 0.5%, 0 to 0.1%, 0 to 0.05%, 0 to 0.03%, 0 to 0.02%, or 0 to 0.01% Compound 4 based on total weight of the composition. In some embodiments, such compositions have 0 to 0.5%, 0 to 0.1%, 0 to 0.05%, 0 to 0.03%, 0 to 0.02%, or 0 to 0.01% Compound 4 based on total weight of the composition. In some embodiments, the compositions have ≤0.02% of Compound 4 based on total weight of the composition.

In some embodiments, such compositions comprise about 0 to 0.04%, about 0 to 0.03%, or about 0 to 0.02% Compound 5 based on total weight of the composition.

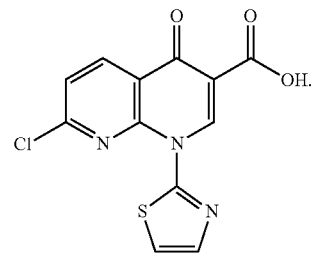

In some embodiments, such compositions consist essentially of 0 to 0.04%, 0 to 0.03%, or 0 to 0.02% Compound 5 based on total weight of the composition. In some embodiments, such compositions have of 0 to 0.04%, 0 to 0.03%, or 0 to 0.02% Compound 5 based on total weight of the composition. In some embodiments, the compositions have ≤0.15% of Compound 5 based on total weight of the composition.

Other compositions that are substantially pure SNS-595 substances are described herein. In some embodiments, such compositions comprise about 0 to 0.5%, about 0 to 0.1%, about 0 to 0.05%, about 0 to 0.03%, about 0 to 0.02%, or about 0 to 0.01% Compound 6 based on total weight of the composition.

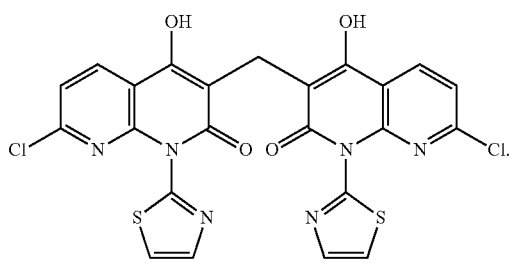

In some embodiments, such compositions consist essentially of about 0 to 0.5%, about 0 to 0.1%, about 0 to 0.05%, about 0 to 0.03%, about 0 to 0.02%, or about 0 to 0.01% Compound 6 based on total weight of the composition. In some embodiments, such compositions have about 0 to 0.5%, about 0 to 0.1%, about 0 to 0.05%, about 0 to 0.03%, about 0 to 0.02%, or about 0 to 0.01% Compound 6 based on total weight of the composition.

In some embodiments, such compositions comprise about 0 to 0.5%, about 0 to 0.1%, about 0 to 0.05%, about 0 to 0.03%, about 0 to 0.02%, or about 0 to 0.01% Compound 7 based on total weight of the composition.

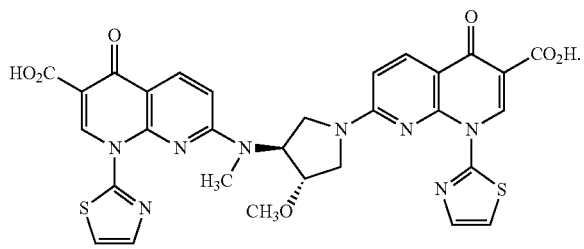

In some embodiments, such compositions consist essentially of about 0 to 0.5%, about 0 to 0.1%, about 0 to 0.05%, about 0 to 0.03%, about 0 to 0.02%, or about 0 to 0.01% Compound 7 based on total weight of the composition. In some embodiments, such compositions have about 0 to 0.5%, about 0 to 0.1%, about 0 to 0.05%, about 0 to 0.03%, about 0 to 0.02%, or about 0 to 0.01% Compound 7 based on total weight of the composition. In some embodiments, the compositions have ≤0.15% of Compound 7 based on total weight of the composition.

As used herein, "SNS-595 substance" refers to a composition comprising SNS-595 and one or more other compounds. In some embodiments, the SNS-595 substance comprises SNS-595 and Compound 4 and/or Compound 5.

As used herein and unless otherwise indicated, "about" refers to up to plus or minus 10% of the indicated value. For example, "about 0.01%" refers to 0.009% to 0.011%, "about 25° C." refers to 22.5° C. to 27.5° C., and "about 0.6 M" refers to 0.54 M to 0.66 M. In some embodiments, about refers to up to plus or minus 9, 8, 7, 6, 5, 4, 3, 2, or 1% of the indicated value. Similarly, for a range of values, use of "about" refers to both the upper limit and the lower limit of the stated range.

The term "about" with respect to a pH value is intended to mean that the acceptable error for that pH value is no greater than 0.01, 0.02, 0.03, 0.04, 0.05, 0.06, 0.07, 0.08, 0.09, or 0.1 pH unit. In certain embodiments, the error for a pH value is no greater than 0.02 pH unit (see, Method 791 in USP XXVI (2003), incorporated herein by reference in its entirety).

As used herein, "aqueous base" refers to any aqueous solution of one or more bases, which, in some embodiments, are one or more strong bases (pKa>13). Examples of strong bases include, without limitation, hydroxides of alkali and alkaline earth metals or ammonium hydroxide. Aqueous bases may be aqueous solutions of organic or inorganic bases. In some embodiments, the base is provided as an aqueous solution of potassium hydroxide, lithium hydroxide, sodium hydroxide, or ammonium hydroxide. In some embodiments, the aqueous base has a molar concentration of about 0.6-1.1 M. In some embodiments, the aqueous base is an aqueous solution of a hydroxide having a molar concentration of about 0.6, 0.7, 0.8, 0.9, 1.0, or about 1.1 M. In some embodiments, the base may be provided in solid form. In some embodiments, the solid form is a pellet or a powder.

As used herein and unless otherwise indicated, the term "hydrate" means a compound or salt thereof, further including a stoichiometric or non-stoichiometric amount of water bound by non-covalent intermolecular forces. As used herein and unless otherwise indicated, the term "solvate" means a solvate formed from the association of one or more solvent molecules to a compound provided herein. The term "solvate" includes hydrates (e.g., monohydrate, dihydrate, trihydrate, tetrahydrate, and the like). The solvates of SNS-595 can be crystalline or non-crystalline.

As used herein, "SNS-595 hydrate" refers to SNS-595 having a stoichiometric or non-stoichiometric amount of water bound by non-covalent intermolecular forces. In some embodiments, the SNS-595 hydrate is crystalline or non-crystalline. In some embodiments, the SNS-595 hydrate comprises about 0.8 to 1.2 molar equivalents of water per mole of SNS-595. In some embodiments, the SNS-595 hydrate comprises about 1 molar equivalent of water per mole of SNS-595.

As used herein, "dehydrating" refers to removing water bound to the SNS-595 of a SNS-595 hydrate. Dehydrating methods are known to those of ordinary skill in the art. In some embodiments, dehydrating is accomplished by contacting the SNS-595 hydrate with a compound capable of removing water bound to the SNS-595 of the SNS-595 hydrate. Such compounds include dehydration solvents. In some embodiments, the solvent is hygroscopic and/or protic. Exemplary solvents include, without limitation, methanol, ethanol, isopropanol, acetone, or others apparent to those of ordinary skill in the art. In some embodiments, the solvent is anhydrous. In some embodiments, the solvent is anhydrous ethanol. In some embodiments, the anhydrous ethanol comprises less than 0.5% water. In a particular embodiment, dehydrating is accomplished by contacting SNS-595 hydrate with anhydrous ethanol at about 25-80° C., about 40-80° C., about 60-80° C., or about 80° C. In some cases, dehydration may be accomplished by thermal means in the absence of a solvent.

The amount of water in a hydrate may be analyzed using a number of techniques as understood in the art. For example, the amount of water may be determined based on the observed weight loss in a thermogravimetric analysis (TGA) thermogram. In addition, the exhaust from a TGA furnace may be coupled to an instrument of chemical analysis, such as a mass spectrometry instrument or an infrared spectroscopy instrument, to confirm the chemical purity of the water vapor emitted upon heating. Water loss may also be quantified by direct gravimetric means such as "Loss on Drying <731>" as described in the U.S. Pharmacopoeia, the entirety of which is incorporated herein by reference. Karl Fischer (KF) analysis may be used to analyze the water content of a hydrate sample. Coulometric KF analysis for water determination may be performed using a Mettler Toledo DL39 Karl Fischer titrator or other equipment. In one method, approximately 14-32 mg of a sample is placed in a KF titration vessel containing HYDRANAL®—Coulomat AD reagent for coulometric KF titration and mixed for 60 seconds to ensure dissolution. The sample is then titrated by means of a generator electrode, which produces iodine by electrochemical oxidation. The analysis is repeated to ensure reproducibility of the measurements.

As used herein, "neutralizing" or "neutralization" refers to the process of adjusting the pH of a solution to neutrality or approximate neutrality, e.g., pH of from 6.0 to 8.0, 7.0 to 8.0, or 7.3 to 7.7.

As used herein, "particulate matter" refers to any matter formed as a result of by-products of a synthetic preparation of SNS-595 that is insoluble or partially soluble in water or an aqueous mixture. In some embodiments, the particulate matter comprises visible particles. Other impurities including particulates such as lint, glass, metal, and the like may be present in the SNS-595 compositions at or below levels permitted for administration to human subjects in the treatment of disease.

As used herein, "visible particles" refers to insoluble or partially soluble solids in a liquid solution, e.g., an aqueous solution, that are visible to a human eye. In some embodiments, the visible particles are visible under natural sunlight, white-light, fluorescent lighting, or incandescent lighting. In further embodiments, the visible particles are visible when observed under lighting having an intensity of 600-7000 lux, 900-4000 lux, 850-4650 lux, or 2000-3750 lux. In some embodiments, the particles are visible when inspected for about 1-60, 1-30, 1-15, 1-10, 1-5, or 5 seconds.

In a particular embodiment, the visible particles are visible when tested according to the method described by European Pharmacopeia 5.0, Section 2.9.20, the entirety of which is incorporated herein by reference. In this method, an apparatus having a viewing station comprising (1) a matt black panel of appropriate size held in a vertical position; (2) a non-glare white panel of appropriate size held in a vertical position next to the black panel; and (3) an adjustable lampholder fitted with a suitable, shaded, white-light source and with a suitable light diffuser (e.g., a viewing illuminator containing two 13 W fluorescent tubes, each 525 mm in length) is used. The intensity of illumination at the viewing point is maintained between 2000 lux and 3750 lux. Higher values may be used for glass and plastic containers. Adherent labels are removed from the container containing the sample to be tested. The outside of the container is washed and dried. The container is gently swirled or inverted while ensuring that air bubbles are not introduced, and the container is observed for about 5 seconds in front of the white panel to determine whether visible particles are present. The container is then observed for about 5 seconds in front of the black panel to determine whether visible particles are present. In some embodiments, the visible particles are visible against a white panel. In some embodiments, the visible particles are visible against a black panel.

In some embodiments the visible particles have an average diameter of at least 50 μm, at least 75 μm, at least 100 μm, at least 150 μm, or at least 200 μm. In some embodiments the visible particles have an average diameter of about 50-500 μm, about 50-300 μm, about 100-500 μm, or about 100-300 μm.

As used herein, "sub-visible particles" refers to particulate matter detectable by the Light Obscuration Particle Count Test or Microscopic Particle Count Test described in the U.S. Pharmacopoeia, <788> Particulate Matter in Injections, which is incorporated herein by reference in its entirety.

In some embodiments, the visible and/or sub-visible particles comprise matter from the production process of a drug substance composition, including, without limitation, the synthesis or formulation of the drug substance, or the packaging of the composition. In some embodiments, the visible particles comprise metal, glass, lint, or the like.

In certain embodiments, the visible and/or sub-visible particles comprise one or more of Compound 5

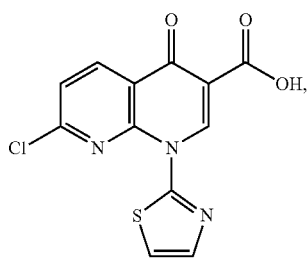

and/or Compound 6

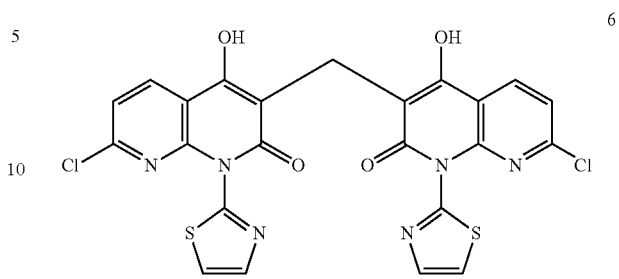

and/or Compound 7

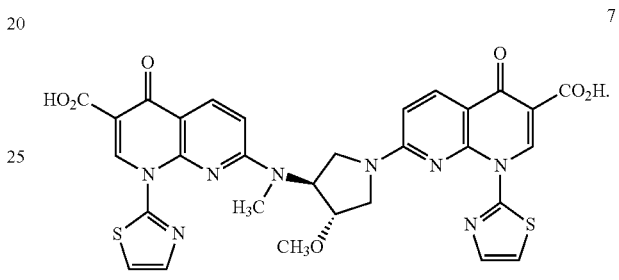

As used herein, "essentially free of visible particles" refers to a liquid, e.g., aqueous, composition comprising SNS-595 that does not contain visible particles. In some embodiments, the composition does not contain visible particles when adjudged by the methods described by European Pharmacopeia 5.0, Section 2.9.20 discussed above.

As used herein, "essentially free of sub-visible particles" refers to a liquid, e.g., aqueous, composition comprising SNS-595 that does not contain sub-visible particles.

As used herein, "stable" refers to a composition comprising SNS-595 that, when stored in a container or vial, can remain essentially free of visible or sub-visible particles, or can maintain a specified amount of visible and/or sub-visible particles, for a specified period of time, e.g., 1, 3, 6 or 9 months. For example, an aqueous composition that is essentially free of visible particles and stable for 6 months with respect to visible particles refers to an aqueous composition that is judged to be essentially free of visible particles at any point in the time during the period starting from a referenced starting point, e.g., the time when the composition was produced and/or added to a container) to 6 months after the composition was prepared. In addition, if the stable composition is a bulk composition, then that composition is capable of being distributed into a lot of containers, e.g., vials, wherein any container containing the distributed composition that is essentially free of visible particles at the time of production of the lot is capable of remaining essentially free of visible particles for the specified period of time, e.g., 1, 3, 6 or 9 months. In some embodiments, the composition is stable for at least 1, 2, 4, 6, 8, 10, 12, 15, 20, or 25 days. In some embodiments, the composition is stable for at least 1, 3, 6, 9, 12, 18, 24, 36, 42, or 48 months. In some embodiments, the composition is stable starting from the time of production.

As used herein, "time of production" refers to the point in time when the SNS-595 composition or container comprising SNS-595 is produced. In some embodiments, "time of production" is the time when the desired amounts of substantially pure SNS-595 substance, sorbitol, water, and methanesulfonic acid are mixed. In other embodiments, the "time of production" is the time when the desired amounts of substantially pure SNS-595 substance, sorbitol, water, and methanesulfonic acid are mixed and added to a container, e.g., vial. In some embodiments, the time is less than 7 days, 6 days, 5 days, 4 days, 3 days, 2 days, or 1 day after the composition or container comprising SNS-595 is produced. In some embodiments, the time is less than 20, 16, 12, 8, 4, or 2 hours after the composition or container comprising SNS-595 is produced.

As used herein and unless otherwise indicated, the term "pharmaceutically acceptable salt" includes, but is not limited to, a salt of an acidic or basic group that can be present in the compounds provided herein. Under certain acidic conditions, the compound can form a wide variety of salts with various inorganic and organic acids. The acids that can be used to prepare pharmaceutically acceptable salts of such basic compounds are those that form salts comprising pharmacologically acceptable anions including, but not limited to, acetate, benzenesulfonate, benzoate, bicarbonate, bitartrate, bromide, calcium edetate, camsylate, carbonate, chloride, bromide, iodide, citrate, dihydrochloride, edetate, edisylate, estolate, esylate, fumarate, gluceptate, gluconate, glutamate, glycollylarsanilate, hexylresorcinate, hydrabamine, hydroxynaphthoate, isethionate, lactate, lactobionate, malate, maleate, mandelate, methanesulfonate (mesylate), methylsulfate, muscate, napsylate, nitrate, pantothenate, phosphate/diphosphate, polygalacturonate, salicylate, stearate, succinate, sulfate, tannate, tartrate, teoclate, triethiodide, and pamoate. Under certain basic conditions, the compound can form base salts with various pharmacologically acceptable cations. Non-limiting examples of such salts include alkali metal or alkaline earth metal salts and, particularly, calcium, magnesium, sodium, lithium, zinc, potassium, and iron salts.

As used herein, "reprocessing" refers to subjecting the SNS-595 (typically obtained from the saponification of Compound 3) to saponification conditions a second time or more. In some embodiments, the SNS-595 is reprocessed more than one time. In some embodiments, the saponification conditions utilize aqueous sodium hydroxide, ethanol, and acetic acid. In some embodiments, the saponification conditions comprise reacting Compound 3 with an aqueous base followed by neutralizing to form SNS-595 hydrate and dehydrating the SNS-595 hydrate.

As used herein, "substantially pure Compound 3" refers a composition consisting essentially of Compound 3

In some embodiments, substantially pure Compound 3 compositions may comprise 0 to 0.3%, 0 to 0.25%, 0 to 0.2%, 0 to 0.1%, 0 to 0.05%, or 0 to 0.01% Compound 1, based on total weight of the composition.

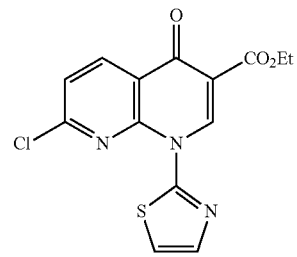

In some embodiments, substantially pure Compound 3 compositions may consist essentially of 0 to 0.3%, 0 to 0.25%, 0 to 0.2%, 0 to 0.1%, 0 to 0.05%, or 0 to 0.01% Compound 1, based on total weight of the composition. In some embodiments, substantially pure Compound 3 compositions may have 0 to 0.3%, 0 to 0.25%, 0 to 0.2%, 0 to 0.1%, 0 to 0.05%, or 0 to 0.01% Compound 1, based on total weight of the composition. In some embodiments, such compositions comprise 0 to 0.1%, or 0 to 0.05%, Compound 1 based on total weight of the composition.

The purity of substantially pure SNS-595 substance or substantially pure Compound 3 provided herein, as well as the amounts of other compounds mentioned herein, can be determined by standard methods of analysis used by those of ordinary skill in the art, such as high performance liquid chromatography (HPLC). In this application, reference to a composition having "0" of any component means that at least the measured amount of that component is lower than the limit of detection using such analytical methods or is 0.001% w/w or less.

4.2 Methods of Preparation

International Patent Application No. WO 2007/146335 and U.S. Provisional Application No. 61/141,856 describe exemplary processes known in the art for the synthesis of the SNS-595 compound. As shown in Scheme 2, this synthesis proceeds via Intermediate 1, which is reacted with Compound 2 in the presence of triethylamine or N,N-diisopropylethylamine to form Compound 3. The ester group of Compound 3 is subsequently hydrolyzed to afford SNS-595.

Scheme 2

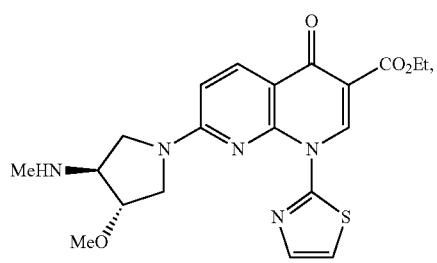

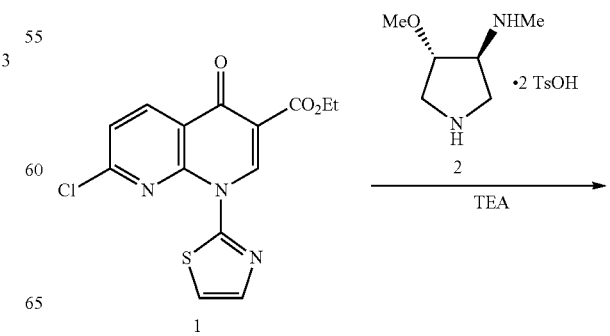

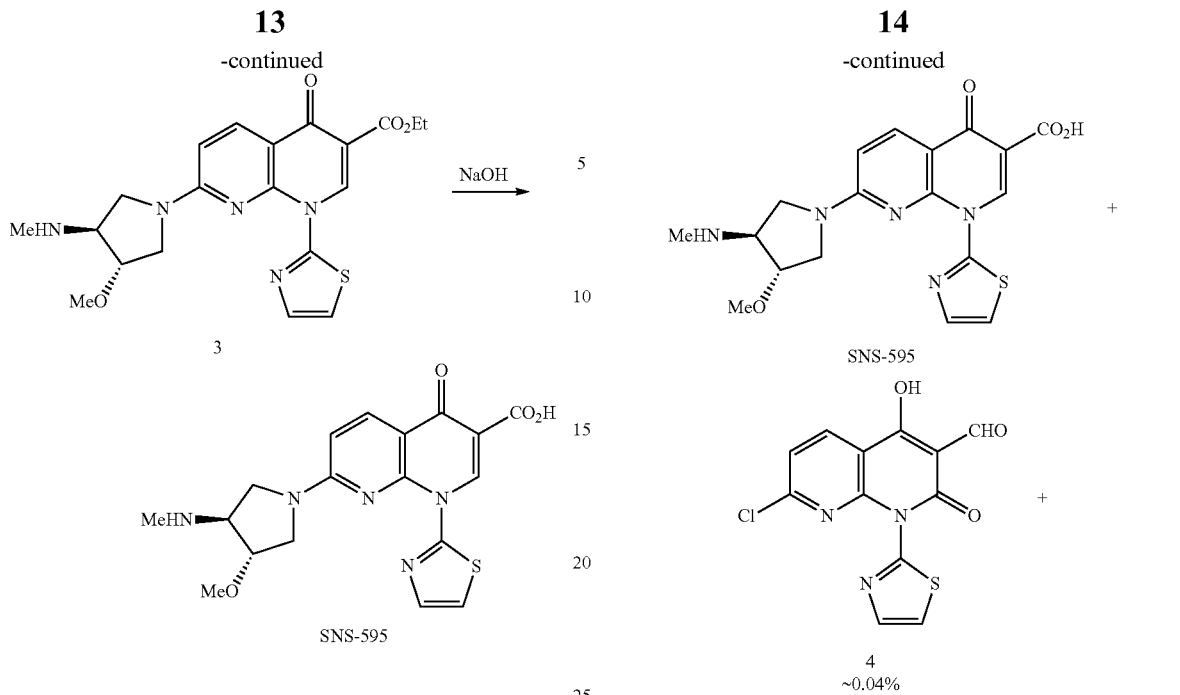

However, when this process is followed, several impurities can be formed. Specifically, as shown in Scheme 3, following saponification of Compound 3 in basic conditions, approximately 0.04% of Compound 4 and <0.05% of Compound 5 can be observed in the reaction product, in addition to SNS-595.

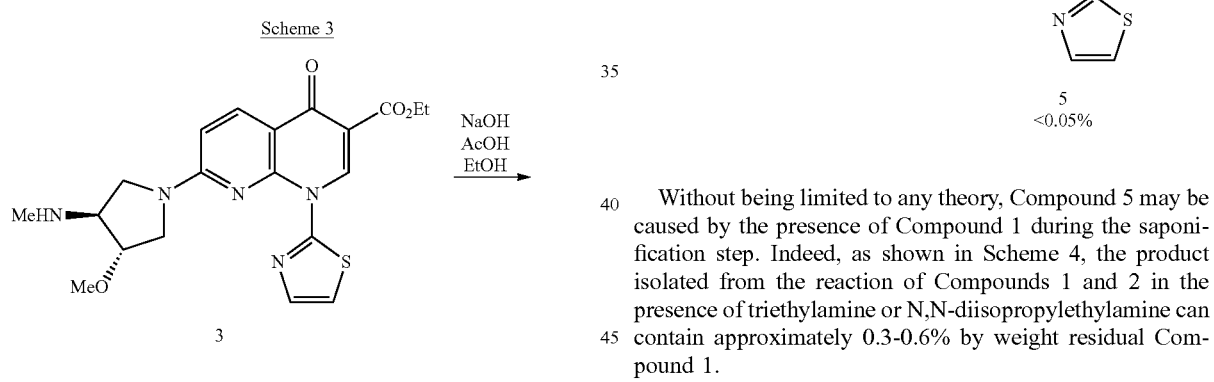

Without being limited to any theory, Compound 5 may be caused by the presence of Compound 1 during the saponification step. Indeed, as shown in Scheme 4, the product isolated from the reaction of Compounds 1 and 2 in the presence of triethylamine or N,N-diisopropylethylamine can contain approximately 0.3-0.6% by weight residual Compound 1.

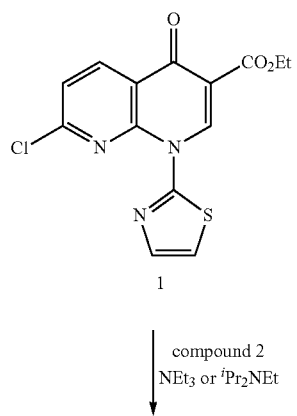

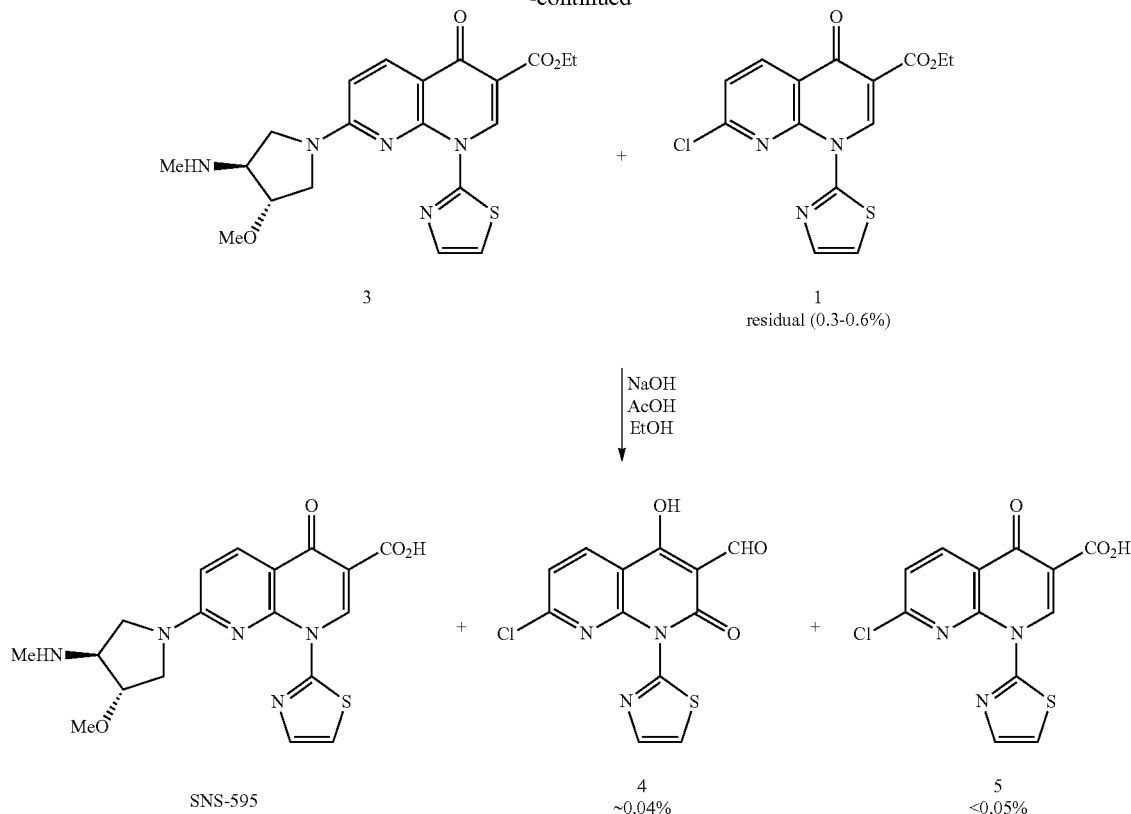

Without being bound to any theory, Compound 4 may be the result of a reaction between Compound 1 and hydroxide, possibly through a 1,4-addition of water. Indeed, when Compound 1 is treated with aqueous sodium hydroxide, Compound 4 can be obtained, in addition to Compound 5, illustrated in Scheme 5.

Scheme 5

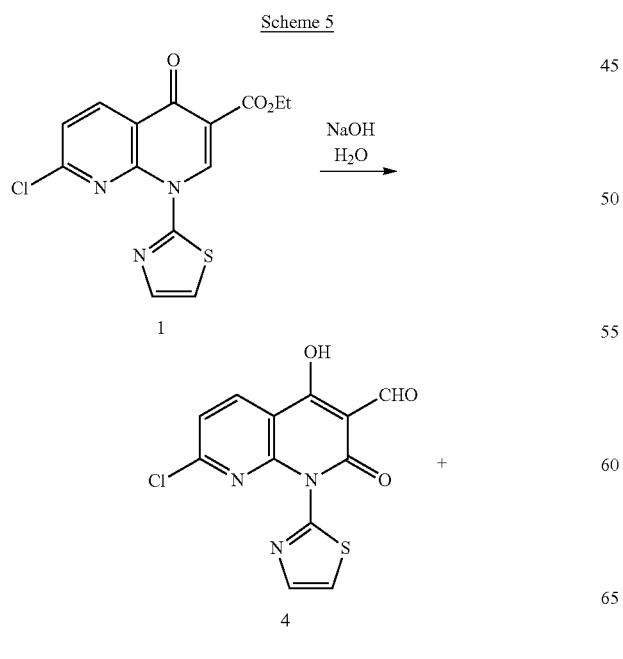

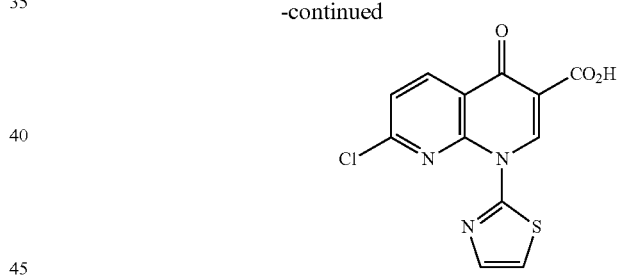

4.2(a) Reprocessing Method

In certain embodiments, processes are provided for preparing substantially pure SNS-595 substance by reprocessing a SNS-595 substance.

As noted, the reaction of Compound 1 with Compound 2 can result in the formation of a mixture of Compound 3 and residual Compound 1. Subsequent treatment of this mixture with aqueous base, i.e., saponification conditions, can result in the formation of a mixture of SNS-595, Compound 4, and Compound 5. However, when this mixture is again subjected to the saponification conditions, i.e., reprocessed, the resulting product can contain SNS-595 with lesser amounts of Compound 4, as shown in Scheme 6.

Scheme 6
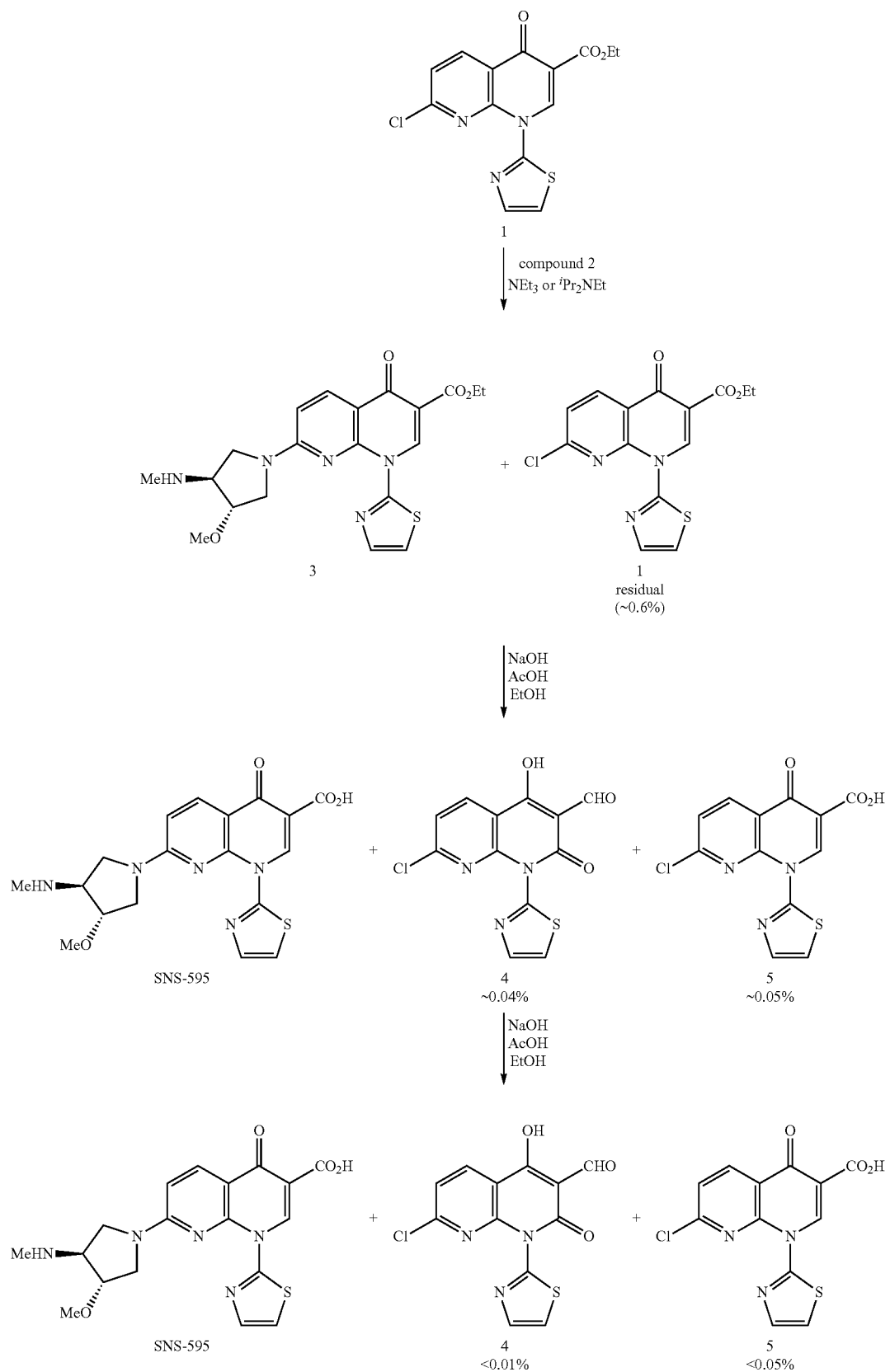

Additional experiments show that several cycles of such reprocessing may be used to sequentially further reduce the residual amount of Compound 4 in the composition. In some embodiments, the reprocessing is performed a number of times sufficient to reduce the level of Compound 4 to below the limit of detection by conventional methods, such as those disclosed herein or in the art.

In certain embodiments, reprocessing is accomplished by solubilizing SNS-595 hydrate with an aqueous base followed by neutralizing with acid, followed by dehydration.

In certain embodiments, provided herein are processes for preparing substantially pure SNS-595 substance comprising:
(a) reacting Compound 3

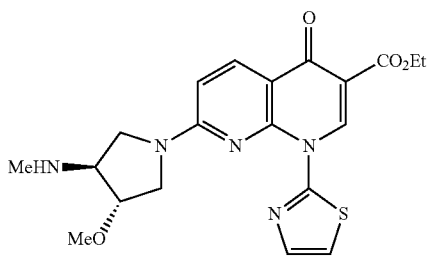

with a first aqueous base followed by neutralizing to obtain a primary SNS-595 hydrate;
(b) dehydrating the primary SNS-595 hydrate from step (a) and reacting the dehydrated product with a second aqueous base followed by neutralizing to obtain a secondary SNS-595 hydrate; and
(c) dehydrating the secondary SNS-595 hydrate obtained in step (b) to obtain substantially pure SNS-595 substance.

The first and second aqueous bases may be the same or different. In some embodiments, the first and second aqueous bases of steps (a) and (b) are each, independently, potassium hydroxide, sodium hydroxide, or lithium hydroxide. In some embodiments, the first and second aqueous bases of steps (a) and (b) are each, independently, sodium hydroxide or lithium hydroxide. In some embodiments, the first and second aqueous bases are each sodium hydroxide. In some embodiments, the first or second aqueous base, each independently, has a molar concentration of about 0.6-1.1 M. In some embodiments, the first or second aqueous base is an aqueous solution of a hydroxide, wherein the first or second aqueous base each independently has a molar concentration of about 0.6, 0.7, 0.8, 0.9, 1.0, or about 1.1 M.

The dehydration steps, independently, may be performed by treatment with dehydration solvents known to those of ordinary skill in the art. For example, dehydration may be accomplished by treating the material to be dehydrated with a hygroscopic and/or protic solvent. Exemplary solvents include, without limitation, ethanol, methanol, isopropanol, and acetone. In some embodiments, the dehydration solvent is anhydrous.

In some embodiments, the SNS-595 hydrate of step (b) or (c) is dehydrated with ethanol. In some embodiments, the ethanol is anhydrous. In particular embodiments, the anhydrous ethanol comprises less than 0.5% water. In some embodiments, the secondary SNS-595 hydrate of step (c) is dehydrated with anhydrous ethanol at a temperature of about 25-80° C., about 40-80° C., about 60-80° C., or about 80° C.

Neutralization steps, independently, may be accomplished with any acid known to those of ordinary skill in the art. Inorganic acids, organic acids, or combinations thereof may be utilized. Acids may also be aqueous. Exemplary acids include, without limitation, acetic acid, hydrochloric acid, hydrobromic acid, sulfuric acid, citric acid, carbonic acid, phosphoric acid, oxalic acid, or nitric acid. In some embodiments, neutralization is accomplished with acetic acid. In some embodiments, the neutralization step adjusts the pH to 6.0 to 8.0. In certain embodiments, pH is adjusted to 7.0 to 8.0. In certain embodiments, pH is adjusted to about 7.3 to 7.7.

In certain embodiments, the first and second aqueous bases of steps (a) and (b) are each sodium hydroxide; pH is adjusted to about 7.3 to 7.7 with acetic acid during neutralization; steps (a) and (b) are performed in the presence of ethanol; and dehydration steps are accomplished with anhydrous ethanol at a temperature between about 25-80° C.

The aqueous base reaction and neutralization may be performed in the presence of organic solvents known to those of ordinary skill in the art. In certain embodiments, the solvent is capable of dissolving SNS-595-hydrate when treated with aqueous base and, at the same time, capable of precipitating SNS-595 hydrate after subsequent neutralization. In some embodiments, step (a) or step (b) is performed in the presence of ethanol or methanol. In some embodiments, step (a) or step (b) is performed in the presence of ethanol. In some embodiments, step (a) and step (b) are each performed in the presence of ethanol. The volume of ethanol or methanol suitable to carry out steps (a) or (b) may be readily determined by those of ordinary skill in the art. In certain embodiments, step (a) or step (b) is performed in the presence of ethanol or methanol, wherein the aqueous base is about 1 to about 20% ethanol or methanol by volume. In particular embodiments, the aqueous base is about 3, 5, 10, or 15% ethanol by volume.

In some embodiments, the substantially pure SNS-595 substance obtained from step (c) comprises about 0 to 0.03% Compound 4 based on total weight of substantially pure SNS-595 substance. In some embodiments, the substantially pure SNS-595 substance obtained from step (c) comprises about 0 to 0.02% Compound 4 based on total weight of substantially pure SNS-595 substance. In some embodiments, the substantially pure SNS-595 substance obtained from step (c) comprises about 0 to 0.01% Compound 4 based on total weight of substantially pure SNS-595 substance. In some embodiments, the substantially pure SNS-595 substance obtained from step (c) comprises about 0 to 0.03%, 0 to 0.02%, or 0 to 0.01% Compound 4 based on total weight of substantially pure SNS-595 substance.

Compound 3 can be obtained by the reaction of Compound 1

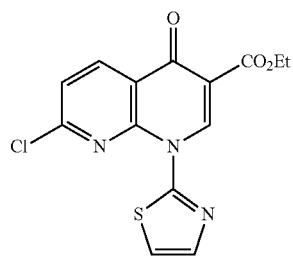

with Compound 2

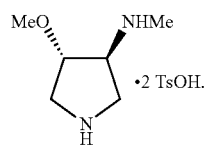

Compound 1 can be prepared or obtained by any source or method deemed suitable by those of ordinary skill in the art. Exemplary methods are described in WO 2007/146335, which is incorporated herein by reference in its entirety.

In some embodiments, Compound 3 is present as a mixture that comprises about 0 to 0.7% of Compound 1, based on total weight of the mixture. In some embodiments, Compound 3 is present as a mixture that comprises about 0 to 0.6% of Compound 1, based on total weight of the mixture. In some embodiments, Compound 3 is present as a mixture that comprises about 0 to 0.3% of Compound 1, based on total weight of the mixture. In some embodiments, Compound 3 is present as a mixture that has 0 to 0.7%, 0 to 0.6%, or 0 to 0.3% Compound 1 based on total weight of the mixture. In some embodiments, Compound 3 is present as a mixture that comprises 0 to 0.7%, 0 to 0.6%, or 0 to 0.3% Compound 1 based on total weight of the mixture. In some embodiments, Compound 3 is present as a mixture that consists essentially of 0 to 0.7%, 0 to 0.6%, or 0 to 0.3% Compound 1 based on total weight of the mixture.

4.2(b) Wet N,N-Diisopropylethylamine Method

In certain embodiments, Compound 1 can be reacted with Compound 2 in the presence of N,N-diisopropylethylamine (DIPEA) and water in acetonitrile to obtain substantially pure Compound 3, which can be subsequently reacted with an aqueous base to obtain substantially pure SNS-595 substance.

When Compound 1 is reacted with Compound 2 in the presence of DIPEA and water in acetonitrile, it can be observed that Compound 3 may be obtained with lower levels of Compound 1 impurity compared to when the reaction is done in the absence of water. As shown in Scheme 7, subsequent saponification with aqueous base can provide SNS-595 having lower levels of both Compound 4 and Compound 5 compared to reaction of Compound 1 with Compound 2 in DIPEA in the absence of water.

Scheme 7

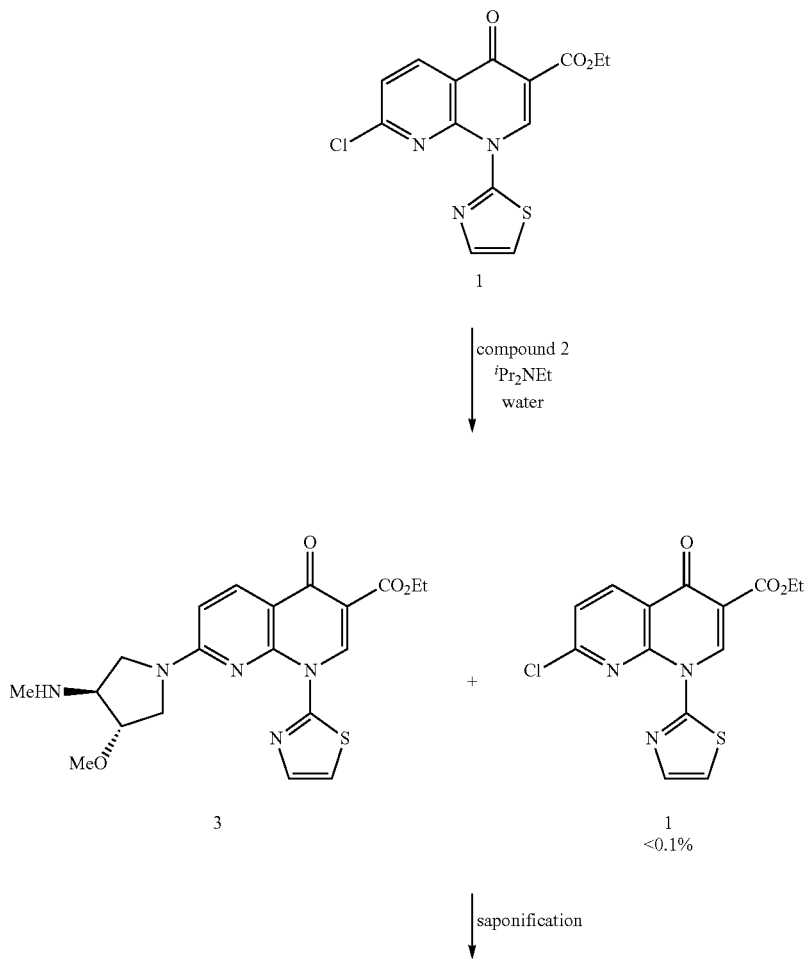

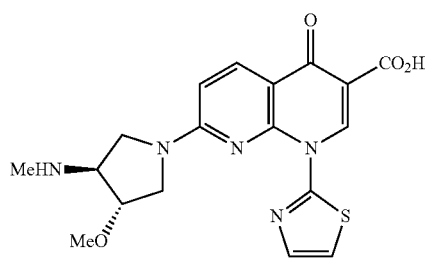

SNS-595

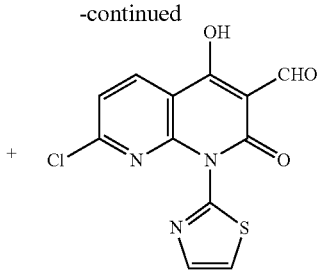

4
~0.01%

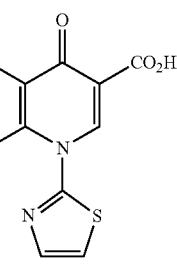

5
<0.02%

In some embodiments, Compound 3

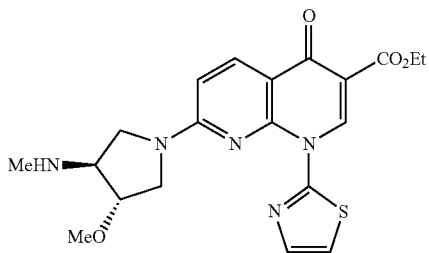

3 is prepared by reacting Compound 1

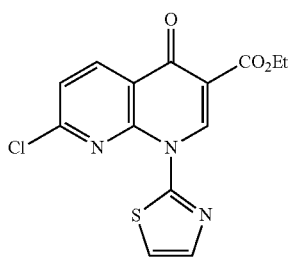

Compound 2

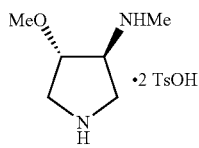

2 in DIPEA and water to obtain Compound 3.

In some embodiments, 0.5% to 10% water in acetonitrile is used. In some embodiments, 2% to 8% water in acetonitrile is used. In some embodiments, 4% to 6% water in acetonitrile is used.

In some embodiments, water can be added at the beginning, during, or at the end of the reaction.

In some embodiments, the process is performed at about 25° C. In some embodiments, the reaction mixture may be heated to effect consumption of Compound 1.

In some embodiments, the process is performed initially at a temperature of about 25° C. and subsequently at a higher temperature. In some embodiments, the higher temperature is below reflux temperature. In a particular embodiment, the temperature at the start of the reaction is 25° C.; such temperature is maintained for a desired time, after which the temperature is raised to about 40-50° C. and maintained at about 40-50° C. for a second desired period. In further embodiments, the process is performed initially at temperature of about 25° C. for about 12 hours (hr) and subsequently at a temperature of about 40-45° C. for about 3-5 hr.

In some embodiments, the substantially pure Compound 3 obtained comprises about 0 to 0.1%, about 0 to 0.05%, or about 0 to 0.03% Compound 1

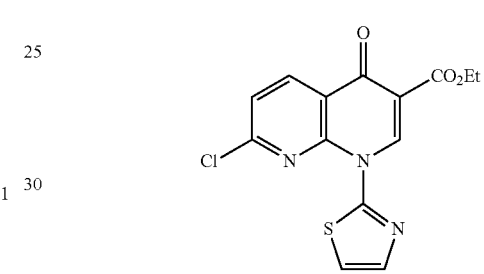

1 based on total weight of substantially pure Compound 3. In some embodiments, the substantially pure Compound 3 obtained comprises 0 to 0.1%, 0 to 0.05%, or 0 to 0.03% Compound 1.

In some embodiments, provided herein are processes for preparing substantially pure SNS-595 substance comprising:

(a) reacting Compound 1

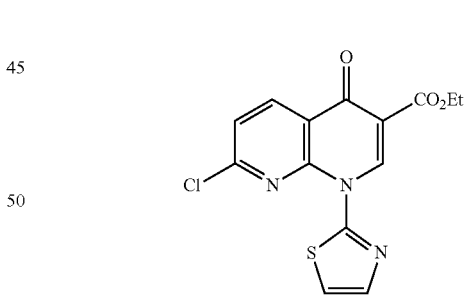

1 with Compound 2

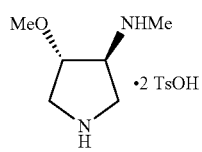

2 in DIPEA and water to obtain substantially pure Compound 3

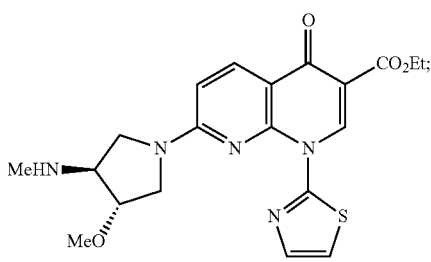

and
(b) reacting the substantially pure Compound 3 with an aqueous base followed by neutralizing to obtain a primary SNS-595 hydrate; and
(c) dehydrating the primary SNS-595 hydrate obtained in step (a) to obtain the substantially pure SNS-595 substance.

In some embodiments, step (a) is performed in the presence of acetonitrile.

In some embodiments, 0.5% to 10% water in acetonitrile is used. In some embodiments, 2% to 8% water in acetonitrile is used. In some embodiments, 4% to 6% water in acetonitrile is used.

In some embodiments, water can be added at the beginning, during, or at the end of the reaction.

In some embodiments, the process is performed at about 25° C. In some embodiments, the reaction mixture may be heated to effect consumption of Compound 1.

In some embodiments, the process is performed initially at a temperature of about 25° C. and subsequently at a higher temperature. In some embodiments, the higher temperature is below reflux temperature. In a particular embodiment, the temperature at the start of the reaction is 25° C.; such temperature is maintained for a desired time, after which the temperature is raised to about 40-50° C. and maintained at about 40-50° C. for a second desired period. In some embodiments, step (a) is performed initially at about 25° C. and subsequently at about 40-45° C. In a particular embodiment, the step (a) is performed initially at about 25° C. for about 12 hr and subsequently at about 40-45° C. for about 3-5 hr. In some embodiments, the step (a) is performed at about 25° C.

In some embodiments, the substantially pure Compound 3 obtained comprises about 0 to 0.1%, about 0 to 0.05%, or about 0 to 0.03% Compound 1

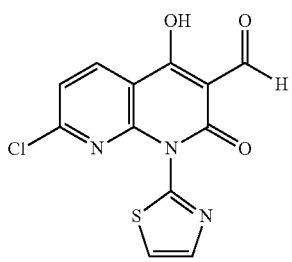

based on total weight of the substantially pure Compound 3. In some embodiments, the substantially pure Compound 3 obtained comprises 0 to 0.1%, 0 to 0.05%, or 0 to 0.03% Compound 1.

In some embodiments, the aqueous base is potassium hydroxide, sodium hydroxide, or lithium hydroxide. In some embodiments, the aqueous base is sodium hydroxide or lithium hydroxide. In some embodiments, the aqueous base is sodium hydroxide. In some embodiments, the aqueous base has a molar concentration of about 0.6-1.1 M. In some embodiments, the aqueous base is an aqueous solution of a hydroxide having a molar concentration of about 0.6, 0.7, 0.8, 0.9, 1.0, or about 1.1 M.

In some embodiments, step (b) is performed in the presence of ethanol or methanol. In some embodiments, step (b) is performed in the presence of ethanol. The volume of ethanol or methanol suitable to carry out step (b) may be readily determined by those of ordinary skill in the art. In certain embodiments, step (b) is performed in the presence of ethanol or methanol, wherein the aqueous base is about 1 to about 20% ethanol or methanol by volume. In particular embodiments, the aqueous base is about 3, 5, 10, or about 15% ethanol by volume.

In some embodiments, an acid is added in step (b) after reacting Compound 3 with the aqueous base to adjust the pH to 6.0 to 8.0. Suitable acids include, but are not limited to acetic acid, hydrochloric acid, sulfuric acid, and the like. In certain embodiments, the acid is acetic acid. In certain embodiments, pH is adjusted to about 7.3 to 7.7.

In certain embodiments, the aqueous base of step (b) is sodium hydroxide; pH is adjusted to about 7.3 to 7.7 with acetic acid after Compound 3 is reacted with the sodium hydroxide in step (b); and step (b) is performed in the presence of ethanol.

In some embodiments, the primary SNS-595 hydrate of step (c) is dehydrated with ethanol. In some embodiments, the ethanol is anhydrous. In particular embodiments, the anhydrous ethanol comprises less than 0.5% water. In some embodiments, the primary SNS-595 hydrate of step (c) is dehydrated with anhydrous ethanol at a temperature of about 25-80° C., about 40-80° C., about 60-80° C., or about 80° C.

In certain embodiments, the substantially pure SNS-595 substance obtained from step (b) comprises about 0 to 0.02% or about 0 to 0.01% Compound 4 based on total weight of substantially pure SNS-595 substance. In some embodiments, the substantially pure SNS-595 substance obtained from step (b) has 0 to 0.02%, or 0 to 0.01% Compound 4. In some embodiments, the substantially pure SNS-595 substance obtained from step (b) consists essentially of 0 to 0.02%, or 0 to 0.01% Compound 4. In some embodiments, the substantially pure SNS-595 substance obtained from step (b) comprises 0 to 0.02%, or 0 to 0.01% Compound 4.

In some embodiments, the substantially pure SNS-595 substance obtained from step (b) comprises about 0 to 0.02% Compound 5

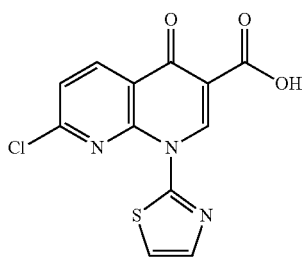

5 based on total weight of substantially pure SNS-595 substance. In some embodiments, the substantially pure SNS-595 substance obtained from step (b) has 0 to 0.02% Compound 5. In some embodiments, the substantially pure SNS-595 substance obtained from step (b) consists essentially of 0 to 0.02% Compound 5. In some embodiments, the substantially pure SNS-595 substance obtained from step (b) comprises 0 to 0.02% Compound 5.

In some embodiments, the substantially pure SNS-595 substance obtained in step (b) is reprocessed. In some embodiments, provided herein are processes for preparing substantially pure SNS-595 substance comprising:

(a) reacting Compound 1

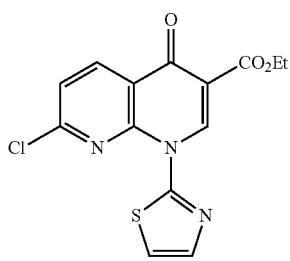

1 with Compound 2

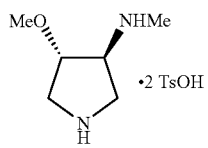

2 in the presence of DIPEA and water to obtain substantially pure Compound 3

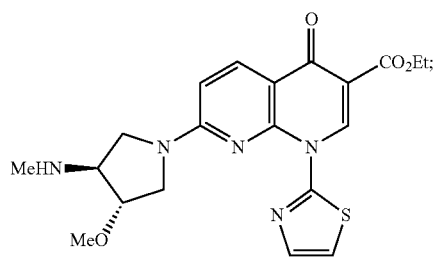

3

(b) reacting substantially pure Compound 3 with a first aqueous base followed by neutralizing to obtain a primary SNS-595 hydrate;

(c) dehydrating the primary SNS-595 hydrate obtained in step (b) to form a SNS-595 substance;

(d) reacting the SNS-595 substance from step (c) with a second aqueous base followed by neutralizing to obtain a secondary SNS-595 hydrate; and (e) dehydrating the secondary SNS-595 hydrate obtained in step (d) to obtain substantially pure SNS-595 substance.

4.3 Compositions

Compositions are provided that comprise substantially pure SNS-595 substance. Compositions are also provided that consist essentially of substantially pure SNS-595 substance. Compositions are also provided that consist of substantially pure SNS-595 substance.

In some embodiments, compositions are provided wherein the substantially pure SNS-595 substance comprises about 0 to 0.03% Compound 4

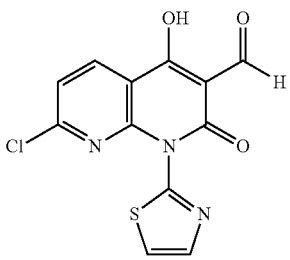

4 based on total weight of substantially pure SNS-595 substance. In some embodiments, the substantially pure SNS-595 substance comprises about 0 to 0.02% or about 0 to 0.01% Compound 4. In some embodiments, the substantially pure SNS-595 substance comprises 0 to 0.03%, 0 to 0.02%, or 0 to 0.01% Compound 4.

In some embodiments, substantially pure SNS-595 substances are provided that consist essentially of SNS-595 and about 0.03 wt % or less, about 0.02 wt % or less, or about 0.01 wt % or less Compound 4. In some embodiments, the composition consists essentially of SNS-595 and 0.03 wt % or less, 0.02 wt % or less, or 0.01 wt % or less Compound 4. In some embodiments, the composition consists of SNS-595 and 0.03 wt % or less, 0.02 wt % or less, or 0.01 wt % or less Compound 4.

In some embodiments, the substantially pure SNS-595 substance comprises about 0 to 0.03%, about 0 to 0.02%, or about 0 to 0.01% Compound 4, at the time of production. In some embodiments, the composition comprises 0 to 0.03%, 0 to 0.02%, or 0 to 0.01% Compound 4, at the time of production.

In some embodiments, substantially pure SNS-595 substances are provided that consist essentially of SNS-595 and about 0.03 wt % or less, about 0.02 wt % or less, or about 0.01 wt % or less Compound 4, at the time of production. In some embodiments, the composition consists essentially of SNS-595 and 0.03 wt % or less, 0.02 wt % or less, or 0.01 wt % or less Compound 4, at the time of production. In some embodiments, the composition consists of SNS-595 and 0.03 wt % or less, 0.02 wt % or less, or 0.01 wt % or less Compound 4, at the time of production.

In some embodiments, compositions are provided wherein the substantially pure SNS-595 substance comprises about 0 to 0.04% Compound 5

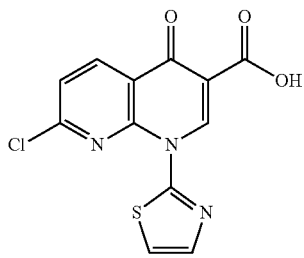

based on total weight of substantially pure SNS-595 substance. In some embodiments, the substantially pure SNS-595 substance comprises about 0 to 0.03%, or about 0 to 0.02% Compound 5. In some embodiments, the substantially pure SNS-595 substance comprises 0 to 0.04%, 0 to 0.03%, or 0 to 0.02% Compound 5.

In some embodiments, substantially pure SNS-595 substances are provided that consist essentially of SNS-595 and about 0.04 wt % or less, about 0.03 wt % or less, or about 0.02 wt % or less Compound 5. In some embodiments, the composition consists essentially of SNS-595 and 0.04 wt % or less, 0.03 wt % or less, or 0.02 wt % or less Compound 5. In some embodiments, the composition consists of SNS-595 and 0.04 wt % or less, 0.03 wt % or less, or 0.02 wt % or less Compound 5.

In some embodiments, the substantially pure SNS-595 substance comprises about 0 to 0.04%, about 0 to 0.03%, or about 0 to 0.02% Compound 5, at the time of production. In some embodiments, the composition comprises 0 to 0.04%, 0 to 0.03%, or 0 to 0.02% Compound 5, at the time of production.

In some embodiments, the substantially pure SNS-595 substance consists essentially of SNS-595 and about 0.04 wt % or less, about 0.03 wt % or less, or about 0.02 wt % or less Compound 5, at the time of production. In some embodiments, the composition consists essentially of SNS-595 and 0.04 wt % or less, 0.03 wt % or less, or 0.02 wt % or less Compound 5, at the time of production. In some embodiments, the composition consists of SNS-595 and 0.04 wt % or less, 0.03 wt % or less, or 0.02 wt % or less Compound 5, at the time of production.

In some embodiments, substantially pure SNS-595 substances are provided wherein the substantially pure SNS-595 substance comprises about 0 to 0.07% total Compound 4 and Compound 5 combined based on total weight of the compositions. In some embodiments, the composition comprises about 0 to 0.05% total Compound 4 and Compound 5 combined. In some embodiments, the substantially composition comprises about 0 to 0.03% total Compound 4 and Compound 5 combined. In some embodiments, the composition comprises 0 to 0.07%, 0 to 0.05%, or 0 to 0.03% total Compound 4 and Compound 5 combined.

In some embodiments, substantially pure SNS-595 substances are provided that consist essentially of SNS-595 and about 0.07 wt % or less, about 0.05 wt % or less, or about 0.03 wt % or less total Compound 4 and Compound 5 combined. In some embodiments, the composition consists essentially of SNS-595 and 0.07 wt % or less, 0.05 wt % or less, or 0.03 wt % or less total Compound 4 and Compound 5 combined. In some embodiments, the composition consists of SNS-595 and 0.07 wt % or less, 0.05 wt % or less, or 0.03 wt % or less total Compound 4 and Compound 5 combined.

In some embodiments, the substantially pure SNS-595 substance comprises about 0 to 0.07%, about 0 to 0.05%, or about 0 to 0.03% total Compound 4 and Compound 5 combined, at the time of production. In some embodiments, the composition comprises 0 to 0.07%, 0 to 0.05%, or 0 to 0.03% total Compound 4 or Compound 5 combined, at the time of production.

In some embodiments, substantially pure SNS-595 substances are provided that consist essentially of SNS-595 and about 0.07 wt % or less, about 0.05 wt % or less, or about 0.03 wt % or less total Compound 4 and Compound 5 combined, at the time of production. In some embodiments, the composition consists essentially of SNS-595 and 0.07 wt % or less, 0.05 wt % or less, or 0.03 wt % or less total Compound 4 and Compound 5 combined, at the time of production. In some embodiments, the composition consists of SNS-595 and 0.07 wt % or less, 0.05 wt % or less, or 0.03 wt % or less total Compound 4 and Compound 5 combined, at the time of production.

The presence of Compound 5 in a solution comprising SNS-595 and water can result in sub-visible microscopic particles. The presence of microscopic or sub-visible particles can be determined by any technique deemed suitable by one of ordinary skill in the art. For instance, the number of particles can be determined by the obscuration method specified in USP-NF General Chapter 788, which is incorporated herein by reference in its entirety and described below. Alternatively, flow imaging techniques (such as that available from Brightwell Technologies, Inc. may be used to determine the particulate matter content of a composition.

In some embodiments, compositions are provided wherein about 100 mg of substantially pure SNS-595 substance is present for every 10 mL of the composition; and wherein the composition has not more than 80, not more than 70, not more than 60, not more than 50, not more than 40, not more than 30, not more than 20, not more than 15, not more than 10, or not more than 5 particles≥25 microns per 10 mL of the composition.

In some embodiments, compositions are provided wherein about 100 mg of SNS-595 is present for every 10 mL of the composition; and wherein the composition has not more than 3000, not more than 2500, not more than 2000, not more than 1500, not more than 1000, not more than 800, not more than 645, not more than 600, not more than 300, or not more than 100 particles≥10 microns per 10 mL of the composition.

In some embodiments, compositions are provided that comprise SNS-595 and 0.3 mg or less, 0.2 mg or less, or 0.1 mg or less Compound 4 per gram of SNS-595. In some embodiments, the compositions are aqueous solutions of a substantially pure SNS-595 substance, e.g., 3 mg or less Compound 4 per 10 gm of the substantially pure SNS-595 substance per 100 mL solution. In some embodiments, the compositions further comprise sorbitol. In some embodiments, the sorbitol is present in an amount providing a 4.5% aqueous solution of sorbitol. In some embodiments, the compositions further comprise methanesulfonic acid. In some embodiments, the methanesulfonic acid is present in an amount to provide the solution a pH of 2.5.

In some embodiments the composition is an aqueous solution consisting essentially of:
  (a) 10 g of a substantially pure SNS-595 substance consisting of SNS-595 and Compound 4, wherein the substantially pure SNS-595 substance contains 0.3 mg or less Compound 4 per gram;
  (b) 4.5 g of sorbitol: and
  (c) sufficient methanesulfonic acid to provide a pH of 2.5;
    per 100 mL of the solution. Also provided are products comprising a container containing an aliquot of such solution, e.g., 10 mL of such solution.

A composition comprising SNS-595 and 0.4 mg or less, 0.3 mg or less, or 0.2 mg or less of Compound 5 per gram of SNS-595. In some embodiments, the compositions are aqueous solutions of a substantially pure SNS-595 substance, e.g., 0.4 mg or less of Compound 5 per 10 gm of the substantially pure SNS-595 substance per 100 mL solution. In some embodiments, the compositions further comprise sorbitol. In some embodiments, the sorbitol is present in an amount providing a 4.5% aqueous solution of sorbitol. In some embodiments, the compositions further comprise methanesulfonic acid. In some embodiments, the methanesulfonic acid is present in an amount to provide the solution a pH of 2.5.

In some embodiments the composition is an aqueous solution consisting essentially of:
(a) 10 g of a substantially pure SNS-595 substance consisting of SNS-595 and Compound 5, wherein the substantially pure SNS-595 substance contains 0.4 mg or less Compound 5 per gram;
(b) 4.5 g of sorbitol: and
(c) sufficient methanesulfonic acid to provide a pH of 2.5; per 100 mL of the solution. Also provided are products comprising a container containing an aliquot of such solution, e.g., 10 mL of such solution.

A composition comprising SNS-595 and 0.7 mg or less total Compound 4 and Compound 5 per gram of SNS-595. A composition comprising SNS-595 and 0.4 mg or less, 0.3 mg or less, or 0.2 mg or less Compound 5 per gram of SNS-595. In some embodiments, the compositions are aqueous solutions of a substantially pure SNS-595 substance, e.g., 4 mg or less of Compound 5 per 10 gm of the substantially pure SNS-595 substance per 100 mL solution. In some embodiments, the compositions further comprise sorbitol. In some embodiments, the sorbitol is present in an amount providing a 4.5% aqueous solution of sorbitol. In some embodiments, the compositions further comprise methanesulfonic acid. In some embodiments, the methanesulfonic acid is present in an amount to provide the solution a pH of 2.5.

In some embodiments the composition is an aqueous solution consisting essentially of:
(a) 10 g of a substantially pure SNS-595 substance consisting of SNS-595, Compound 4, and Compound 5, wherein the substantially pure SNS-595 substance contains 0.7 mg or less total Compound 4 and Compound 5 combined per gram;
(b) 4.5 g of sorbitol: and
(c) sufficient methanesulfonic acid to provide a pH of 2.5; per 100 mL of the solution. Also provided are products comprising a container containing an aliquot of such solution, e.g., 10 mL of such solution.

Further, the presence of Compound 4 in a solution comprising SNS-595 and water can result in the formation of visible particles. Without being limited to any theory, the visible particles can comprise Compound 6 which can be derived from Compound 4. Without being limited to any theory, Compound 4, when exposed to formaldehyde, can react to form Compound 6. Indeed, when Compound 4 is treated with formaldehyde, the formation of Compound 6 has been observed.

In some embodiments, processes are provided that, when compared to processes known in the art, produce substantially pure SNS-595 substance including lower amounts of Compounds 4 and 5, and, thus, lower amounts of particles, e.g., Compound 6, when such substantially pure SNS-595 substance is provided in an aqueous solution.

In some embodiments, processes are provided that, when compared to processes known in the art, produce substantially pure SNS-595 substance including lower amounts of compound 7

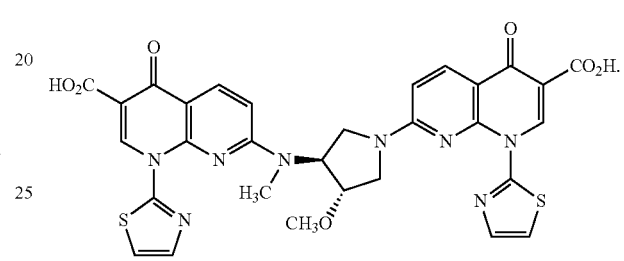

7

In some embodiments, compositions comprising substantially pure SNS-595 substance are provided, wherein the compositions are essentially free of visible particles and are stable over time. In some embodiments, the composition is stable for 1, 2, 4, 6, 8, 10, 12, 15, 20, or 25 day(s). In some embodiments, the composition is stable for 1, 3, 6, 9, 12, 18, 24, 36, or 42 month(s). In some embodiments, the composition is stable starting from the time of production. In some embodiments, the composition is stable when contacted with formaldehyde. In some embodiments, the composition o is stable when contacted with a compound capable of transforming Compound 4

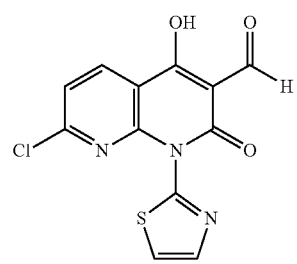

4 to Compound 6

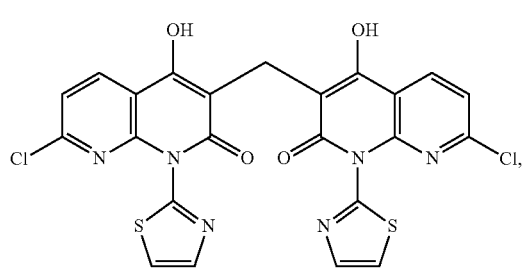

6

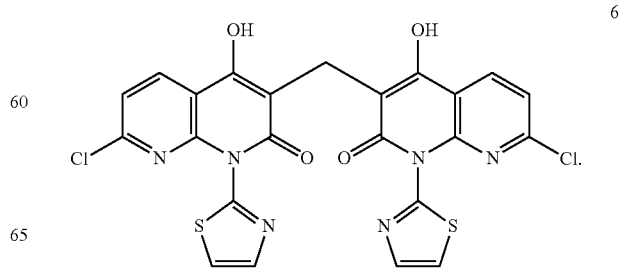

6

As discussed, visible particles may have, in some embodiments, an average diameter of at least 50 μm, at least 75 μm, at least 100 μm, at least 150 μm, or at least 200 μm. In some embodiments the visible particles have an average diameter of about 50-500 μm, about 50-300 μm, about 100-500 μm, or about 100-300 μm.

The crystallinity and crystalline habit may be determined using methods known to those of ordinary skill in the art. For example, crystallinity and crystalline habit may be assessed by polarized light microscopy. In some embodiments, the visible particles are crystalline powders. In some embodiments, the crystalline habit of the visible particles is that of plates about 45 μm to about 150 μm, or about 50 μm to about 100 μm.

The detection of visible particles in a composition can be determined by any technique deemed suitable by one of ordinary skill in the art. For instance, visible particles may be detected by the method specified in European Pharmacopeia 5.0, section 2.9.20, which is incorporated herein by referenced in its entirety. Certain exemplary techniques are described in greater detail below.

In some embodiments, visible particle presence is determined at an illumination intensity between about 2000 and 3750 lux.

In some embodiments, the visible particles comprise compound 6.

In some embodiments, the visible particles comprise compound 7.

In some embodiments, processes are provided that, when compared to processes known in the art, produce substantially pure SNS-595 substance including lower amounts of sub-visible particles as detected by the Light Obscuration Particle Count Test as described in the U.S. Pharmacopoeia, <788> Particulate Matter in Injections, the entirety of which is incorporated herein by reference. In some embodiments, the sub-visible particles comprise one or more of compounds 5, 6, and/or 7.

In some embodiments, provided herein are compositions comprising substantially pure SNS-595 substance, wherein the compositions contain not more than 6000 sub-visible particles≥10 μm per vial, not more than 3000 sub-visible particles≥10 μm per vial, or not more than 1000 sub-visible particles≥10 μm per vial as measured by light obscuration. In some embodiments, provided herein are compositions comprising substantially pure SNS-595 substance, wherein the compositions contain not more than 600 sub-visible particles≥25 μm per vial, not more than 300 sub-visible particles particles≥25 μm per vial, or not more than 100 sub-visible particles≥25 μm per vial by light obscuration. In some embodiments, provided herein are compositions comprising substantially pure SNS-595 substance, wherein the compositions contain not more than 3000 sub-visible particles≥10 μm per vial, not more than 1500 sub-visible particles≥10 μm per vial, or not more than 300 sub-visible particles≥10 μm per vial as measured by microscopic evaluation. In some embodiments, provided herein are compositions comprising substantially pure SNS-595 substance, wherein the compositions contain not more than 300 sub-visible particles≥25 μm per vial, not more than 150 sub-visible particles≥25 μm per vial, or not more than 30 sub-visible particles≥25 μm per vial as measured by microscopic evaluation.

In some embodiments, the composition comprises sorbitol. In further embodiments, the composition comprises methanesulfonic acid. In further embodiments, the sorbitol is present in an amount providing a 4.5% aqueous solution of sorbitol. In some embodiments, the methanesulfonic acid is present in an amount to provide a pH of 2.5. In some embodiments, the composition is stable.

In some embodiments, the composition consists essentially of 100 mg substantially pure SNS-595 substance, 450 mg of D-sorbitol, water, and methanesulfonic acid, wherein the methanesulfonic acid is present in amount to provide a pH of 2.5, and wherein the water is present in an amount to provide a total composition volume of 10 mL. In some embodiments, the composition is stable.

In some embodiments, the composition consists essentially of water, substantially pure SNS-595 substance, sorbitol, and methanesulfonic acid. In some embodiments, the composition is stable.

In some embodiments, compositions consisting essentially of SNS-595 and 0.03 wt % or less Compound 4 are provided.

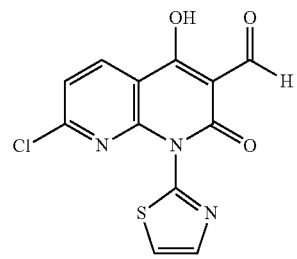 [SMILES: O=Cc1c(O)c2ccc(Cl)nc2n(-c2nccs2)c1=O]

4

In some embodiments, compositions consisting essentially of SNS-595 and 0.04 wt % or less Compound 5 are provided.

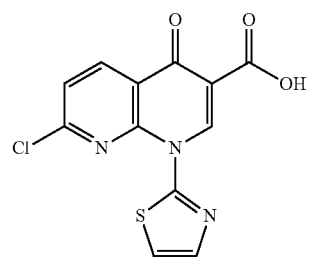

5

In some embodiments, compositions consisting essentially of SNS-595 and 0.07 wt % or less total Compound 4 and Compound 5 are provided.

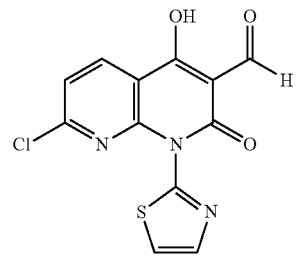

4

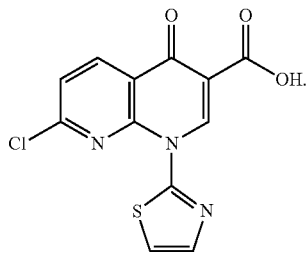

5

In some embodiments, compositions comprising SNS-595 and 0.3 mg or less Compound 4 per gram of SNS-595 are provided.

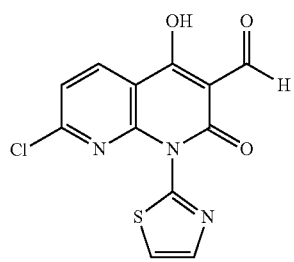

4

In some embodiments, compositions comprising SNS-595 and 0.4 mg or less Compound 5 per gram of SNS-595 are provided.

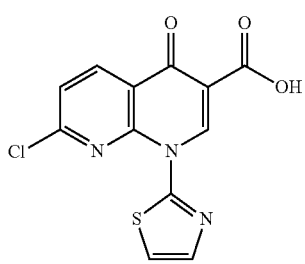

5

In some embodiments, compositions comprising SNS-595 and 0.7 mg or less total Compound 4 and Compound 5 per gram of SNS-595 are provided.

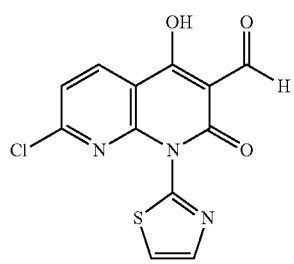

4

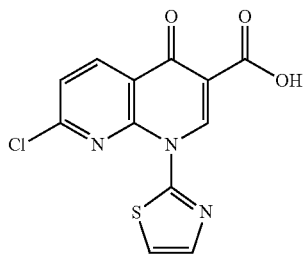

5

In some embodiments, compositions consisting essentially of:
(a) 10 g of a substantially pure SNS-595 substance consisting of SNS-595 and Compound 4 wherein the substantially pure SNS-595 substance contains 3 mg or less Compound 4 per gram

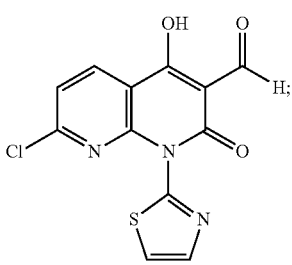

4

(b) 4.5 g of sorbitol: and
(c) sufficient methanesulfonic acid to provide a pH of 2.5; per 100 mL of the solution are provided. In some embodiments, a product comprising a container containing 10 mL of such solution is provided.

In some embodiments, an aqueous solution consisting essentially of:
(a) 10 g of a substantially pure SNS-595 substance consisting of SNS-595 and Compound 5

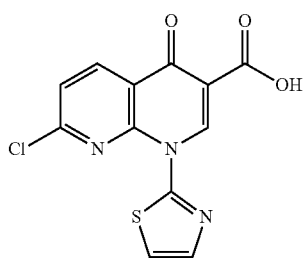

5 wherein the substantially pure SNS-595 substance contains 4 mg or less Compound 5 per gram;
(b) 4.5 g of sorbitol: and
(c) sufficient methanesulfonic acid to provide a pH of 2.5; per 100 mL of the solution is provided. In some embodiments, a product comprising a container containing 10 mL of such solution is provided.

In some embodiments, an aqueous solution consisting essentially of:
(a) 10 g of a substantially pure SNS-595 substance consisting of SNS-595, Compound 4 and Compound 5

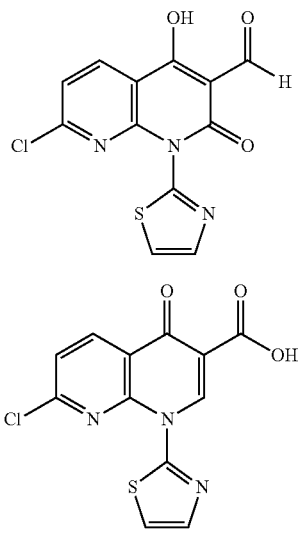

wherein the substantially pure SNS-595 substance contains 7 mg or less total Compound 4 and Compound 5 combined per gram;
(b) 4.5 g of sorbitol: and
(c) sufficient methanesulfonic acid to provide a pH of 2.5; per 100 mL of the solution is provided. In some embodiments, a product comprising a container containing 10 mL of such solution is provided.
Also provided herein is a compound of formula 6

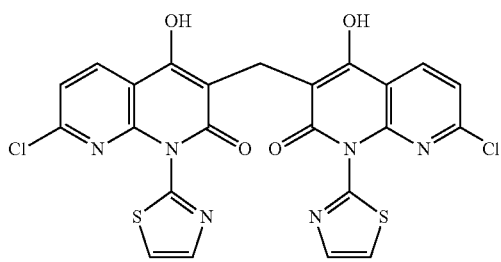

or a pharmaceutically acceptable salt thereof.

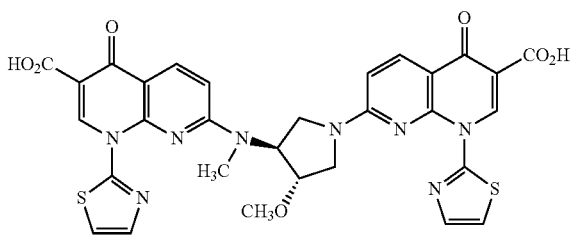

or a pharmaceutically acceptable salt thereof.

6. EXAMPLES

Certain embodiments of the claimed subject matter are illustrated by the following non-limiting examples.

Example 1

Reduction of Compound 4 by Reprocessing

As noted, the reaction of Compound 1 with Compound 2 can result in the formation of a mixture of Compound 3 and residual Compound 1. Subsequent treatment of this mixture with aqueous base, i.e., saponification conditions with, for example, aqueous sodium hydroxide, can result in the formation of a mixture of SNS-595, Compound 4, and Compound 5. However, when this mixture is again subjected to the saponification conditions, i.e., reprocessed, the resulting product can contain SNS-595 with lower amounts of Compound 4, as seen above in Scheme 6.

Experiments were performed to assess the effect of such reprocessing of SNS-595 substance on the residual levels of Compound 4. The results of these experiments are presented in Table 1.

TABLE 1

Reduction of Compound 4 by reprocessing

| Experiment | Entry | Scale | Compound 4 spiked (actual) wt % | Compound 4 after NaOH treatment area % | Compound 4 after reprocessing area % (wt %) |
|---|---|---|---|---|---|
| 1 | 1 | 1 g | 1 | 0.70 | 0.06 |
|  | 2 |  | None | 0.06 | <0.01 |
|  | 3 |  |  | <0.01 | <0.01 |
| 2 | 4 | 1 g | 1 | 0.89 | 0.06 |
|  | 5 |  | None | 0.06 | ND |
| 3 | 6 | 25 g | 0.3 | NA | 0.01 (0.033) |
| 4 | 7 | 25 g | 0.2 | NA | 0.005 (0.015) |
| 5 | 8 | 25 g | 0.1 | NA | 0.002 (0.003) |
| 6 | 9 | 40 g | 0.02 [1] | NA | (0.004) |
| 7 | 10 | 200 g | 0.02 [1] | NA | (0.005) |
| 8 | 11 | 1.49 kg | 0.02 [1] | NA | (<0.005) |
| 9 | 12 | 1.2 kg | 0.02 [1] | NA | (<0.015) |

[1] SNS-595 with 0.02% Compound 4 was used
NA = not available; ND = None detected

Experiment 1

To a solution of sodium hydroxide (0.15 g) in water (5 mL), SNS-595 (0.98 g), Compound 4 (0.010 g) and ethanol (EtOH) (1 mL) were added. The mixture was filtered and the HPLC analysis of the filtrate showed Compound 4 as about 0.7% (by area). The pH of the filtrate was adjusted to 6 by slow addition of acetic acid and the solution was heated to precipitate SNS-595 hydrate. The slurry was cooled and filtered to give SNS-595 hydrate. HPLC analysis of the solid showed it to have 0.06% (by area) of Compound 4, indicating that a ~10-fold reduction in Compound 4 had occurred. The solid was re-subjected to reprocessing using aqueous sodium hydroxide (0.18 g in 6 mL water) and EtOH (1 mL), followed by pH adjustment with aqueous acetic acid. After heating, the solid was filtered to give SNS-595 hydrate having less than 0.01% Compound 4, demonstrating at least a further six-fold reduction in the amount of the contaminant.

Experiment 2

SNS-595 (~1 g) was spiked with 1% Compound 4. HPLC analysis of this spiked sample following reprocessing conditions, i.e., treatment with NaOH, showed 0.89% Compound 4 by area. This material was then pH-adjusted and the solid isolated as above. HPLC analysis showed 0.06% Compound 4 by area, indicating that a ~10-fold reduction in Compound 4 occurred, consistent with the first experiment above.

This material, when again subjected to reprocessing conditions, provided a SNS-595 substance with no detectable Compound 4, demonstrating at least a six-fold reduction in the amount of that contaminant.

Scalability Experiments:

Experiments 3-9 were performed to evaluate the scalability of this process. The procedure for Experiment 8 is provided as an exemplary procedure. Results for Experiments 3-9 are summarized below and on Table 1.

Exemplary Procedure for Large Scale Reprocessing (Experiment 8):

To a solution of NaOH (0.2 kg) in water (4.8 kg), SNS-595 (1.49 kg) having Compound 4 (~0.24% by weight) was added. To the mixture, EtOH (0.13 kg) was added. The solution was filtered and the pH of the filtrate was adjusted to 7.3-7.7 by slow addition of aqueous acetic acid. The mixture was heated to 55-65° C., cooled, and filtered. The filter cake was washed with water, EtOH and dried under vacuum to give a SNS-595 hydrate (1.36 kg) having 0.013% (by weight) Compound 4. The hydrate (1.36 kg) was dehydrated by slurrying in EtOH (23 kg) at 67-78° C. After cooling, the mixture was filtered, washed with EtOH and dried at 65-75° C. under vacuum to give a SNS-595 substance (1.0 kg) having less than 0.005% Compound 4.

Summary of Scalability Experiments:

In Experiment 3, 25 g of SNS-595 having 0.3% Compound 4 was subjected to reprocessing conditions, i.e., sodium hydroxide, followed by pH adjustment and dehydration. HPLC analysis of resulting SNS-595 showed 0.01% Compound 4 by area, indicating that a ~30 fold reduction in Compound 4 had occurred.

In Experiment 4, 25 g of SNS-595 having 0.2% Compound 4 was subjected to reprocessing conditions, i.e., sodium hydroxide, followed by pH adjustment and dehydration. HPLC analysis of resulting SNS-595 showed 0.005% Compound 4 by area, indicating that a ~40 fold reduction in Compound 4 had occurred.

In Experiment 5, 25 g of SNS-595 having 0.1% Compound 4 was subjected to reprocessing conditions, i.e., sodium hydroxide, followed by pH adjustment and dehydration. HPLC analysis of resulting SNS-595 showed 0.002% Compound 4 by area, indicating that a ~50 fold reduction in Compound 4 had occurred.

In Experiment 6, 40 g of SNS-595 having 0.02% Compound 4 was subjected to reprocessing conditions, i.e., sodium hydroxide, followed by pH adjustment and dehydration. HPLC analysis of resulting SNS-595 showed 0.004% Compound 4 by area, indicating that a ~5-fold reduction in Compound 4 had occurred.

In Experiment 7, 200 g of SNS-595 having 0.02% Compound 4 was subjected to reprocessing conditions, i.e., sodium hydroxide, followed by pH adjustment and dehydration. HPLC analysis of resulting SNS-595 showed less than 0.005% Compound 4 by area, indicating that a ~4-fold reduction in Compound 4 had occurred.

In Experiment 8, 1.49 kg of SNS-595 having 0.02% Compound 4 was subjected to reprocessing conditions, i.e., sodium hydroxide, followed by pH adjustment. HPLC analysis showed <0.005% Compound 4 by area, indicating that a ~4 fold reduction in Compound 4 occurred.

In Experiment 9, 1.2 kg of SNS-595 having 0.02% Compound 4 was subjected to reprocessing conditions, i.e., sodium hydroxide, followed by pH adjustment and dehydration. HPLC analysis of resulting SNS-595 showed <0.015% Compound 4 by area, indicating that a ~2-fold reduction in Compound 4 had occurred.

Example 2

Reduction of Amount of Compound 6

As discussed, the presence of Compound 4 in a SNS-595 solution may be attended by the formation of visible particles, which, without being limited to any theory, comprise Compound 6. Experiments were performed to assess the effect of reducing Compound 4 levels on the formation of Compound 6 over time.

Four different sample drug product solutions were prepared from the drug substances having varying levels of Compound 4 outlined in Table 2, below. Sample 1 used the reprocessed product obtained from Experiment 6 (described in Example 1) and had <0.005% Compound 4. Whenever external addition of Compound 4 was made, Compound 4 was first dissolved in a 5 mM aqueous NaOH solution. A total of 2% of the aqueous NaOH solution was added to each of the drug product Samples for consistency purposes.

Figure 1:
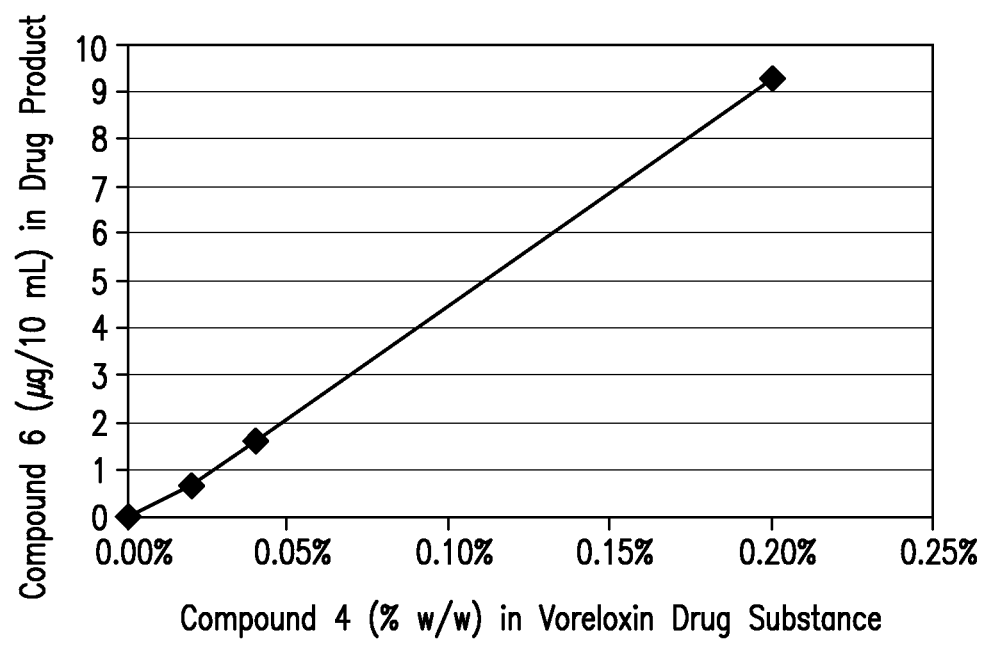

The various drug product Samples were filtered twice through a 0.22 μm PVDF SteriCup filters. These pre-autoclaved, filtered drug product Samples were analyzed for their Compound 4 content six days following preparation and storage at room temperature (RT) shielded from light. FIG. 1 and Table 2 show that the amount of Compound 6 in the drug product correlated directly with the level of Compound 4 in the SNS-595 drug substance.

The filtered drug product Samples were then filled in 30 mL Schott glass vials and stoppered. Vial filling and stoppering were performed in a laminar flow hood. Vials and stoppers used in this study were rinsed with filtered water and allowed to dry in the laminar flow hood before use. Vials were not depyrogenated and stoppers were not sterilized before use. Filled and stoppered vials were crimp-sealed, autoclaved, and stored upright and shielded from light at 40° C./75% relative humidity (RH). After 65 days of storage, the vials were inspected for the presence of visible particles and analyzed by HPLC for Compound 6 content. Analysis of the Samples having less than 0.01% Compound 4 (entry 1) showed that the resulting drug product had no visible particles and no detectable amount of Compound 6 after 65 days. Experiments with Samples having ≥0.02% Compound 4 showed significant formation of Compound 6 and visible particles during the same time period (Samples 2-4). The amount of Compound 6 after 65 days correlated directly with the initial amount of Compound 4 in the SNS-595 substance.

TABLE 2

Effect of Compound 4 on Compound 6 levels

| Sample | Nominal Compound 4 in Drug Substance (% w/w) | Compound 6 (μg/vial) After ~6 days | Compound 6 (μg/vial) After 65 days |
|---|---|---|---|
| 1 | <0.01 | 0.0 | 0.0 |
| 2 | 0.02 | 0.6 | 7-9 |
| 3 | 0.04 | ~2 | 14-19 |
| 4 | 0.20 | ~9 | 16-24 |

Example 3

Reduction of Compounds 4 and 5 by Via Wet DIPEA

Experiments were performed to assess the effect of water on the reaction between Compound 1 and Compound 2 in the presence of DIPEA. Experiments were also performed to compare the effect of adding water during the beginning of the reaction with adding water at the end of the reaction.

When Compound 1 and Compound 2 were reacted at 40-45° C. in the absence of water, analysis of the product showed between 0.26% and 0.31% residual Compound 1 by area.

In a second series of experiments, Compound 1 and Compound 2 were reacted at RT for 12 hr, and subsequently heated to 40-45° C. for 3-5 hr. In these experiments, water was added at the beginning of the reaction. Analysis of the product showed between 0.01% and 0.08% residual Compound 1 by area.

In a third series of experiments, Compound 1 and Compound 2 were reacted at RT for 12 hr, and subsequently heated to 45° C. for 3 hr. In these experiments, water was added at the end of the reaction. Analysis of the product showed 0.03% to 0.09% residual Compound 1 by area.

The experiments above are summarized in the table below.

TABLE 3

Effect of water in SNS-595 synthesis

| Rxn Condition | Water (volume) | Scale | Residual Compound 1 (area %)* | Comments |
|---|---|---|---|---|
| DIPEA, 40-45° C. | 0 | 50 g | 0.26 0.31 | No water |
| DIPEA, RT, 12 hr, then heated to 40- 45° C., 3-5 hr | 0.5 | 1 g 10 g 50 g 100 g 1 kg | 0.05 0.08 0.08 0.05 0.01 | Water added at the beginning |
| DIPEA, RT, 12 hr, then heated to 40- 45° C., 3 hr | 0.5 | 10 g 10 g 50 g 100 g | 0.03 0.05 0.09 0.07 | Water added after 12 hr at RT |

*Analyzed at 275 nm

The following is an exemplary procedure for the experiments described in the Table 3 above.

To a slurry of Compound 2 (1.55 kg) in acetonitrile (ACN; 10 L), DIPEA (4 L) and water (0.5 L) were added. To the solution, Compound 1 (1 kg) and ACN (1 L) were added and the reaction was stirred for about 12 hr at RT. The reaction mixture was then heated to about 45° C. for about 2-6 hr. After cooling, the product was filtered, washed with ACN (4 L) and dried under vacuum to give Compound 3 (1.1 kg). HPLC analysis showed this material to contain <0.1% Compound 1.

Experiments were carried out to determine the impact of residual Compound 1 levels on the Compound 4 levels resulting during the manufacture of SNS-595. These experiments demonstrated a correlation between Compound 1 levels in Compound 3 and Compound 4 levels in the resulting SNS-595 substance. Experiments at laboratory scale also demonstrated that using Compound 3 substance having <0.1% Compound 1 provided a SNS-595 substance with <0.01% Compound 4. The results of these experiments are summarized below in Table 4 and FIG. 2.

TABLE 4

Impact of residual Compound 1 in Compound 3 on Compound 4 levels in SNS-595

| Entry | Scale | Compound 1 Area % | Compound 4 (wt %) |
|---|---|---|---|
| 1 | 0.15 kg | 0.50 | 0.04 |
| 2 | 0.75 kg | 0.60 | 0.05 |
| 3 | 2.1 kg | 0.64 | 0.04 |
| 4 | 5 g | 0.24 | 0.02 |
| 5 | 10 g | 0.08 | 0.007 |
| 6 | 50 g | 0.09 | 0.008 |
| 7 | 1 kg | 0.01 | <0.005 |

The following is an exemplary procedure for the experiments described in Table 4 above.

Compound 3 (0.9 kg) (having <0.1% Compound 1) was added to a solution of sodium hydroxide (0.14 kg) in water (3.3 kg) and EtOH (0.16 L). The mixture was stirred for about 12 hr and filtered to remove insoluble materials. The pH of the filtrate was adjusted to 7.3-7.7 with aqueous acetic acid. The resulting mixture was heated to about 60° C. for 2-4 hr, cooled and filtered. The filter cake was washed with water, EtOH and dried under vacuum. The resulting SNS-595 hydrate was slurried in EtOH (20 L) at about 70° C. for about 4 hr, cooled and filtered. The filter cake was washed with EtOH and dried at 55-75° C. under vacuum to give SNS-595 substance (0.66 kg) having less than 0.005% Compound 4 (Table 4, entry 7).

Figure 3:
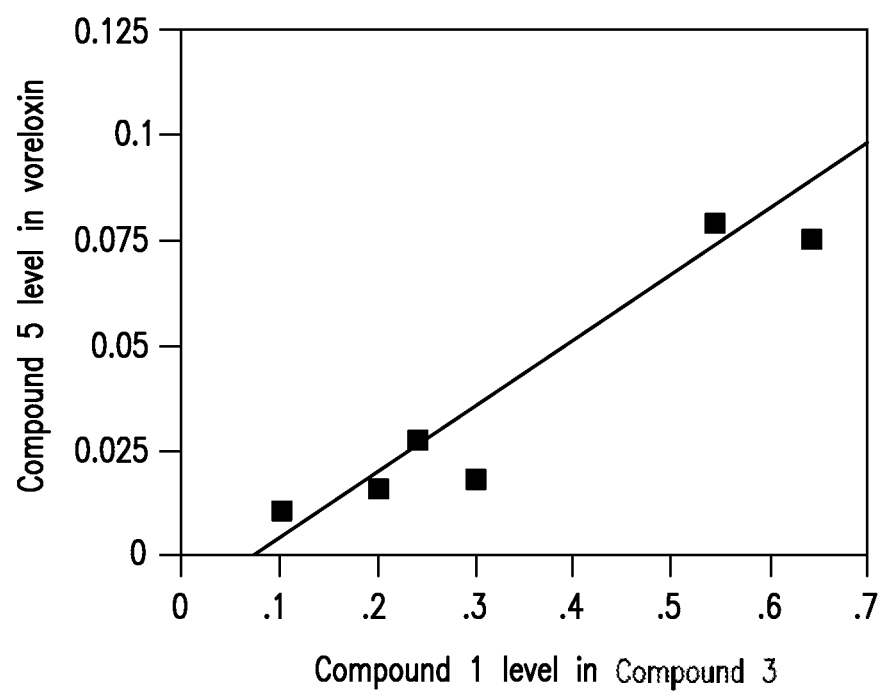
FIG. 3 illustrates the observed relationship between the amount of Compound 5 in SNS-595 drug substance and the amount of residual Compound 1 in Compound 3 used to prepare the drug substance.

In a similar manner, experiments were carried out to determine the impact of residual Compound 1 levels on the Compound 5 levels in SNS-595. These experiments demonstrated a correlation between Compound 1 levels in Compound 3 and Compound 5 levels in SNS-595. The results of these experiments are summarized below in Table 5 and FIG. 3.

TABLE 5

Impact of residual Compound 1 on Compound 5 levels in SNS-595

| Entry | Scale | Compound 1 (Area %) | Compound 5 (wt %) |
|---|---|---|---|
| 1 | 0.75 kg | 0.60 | 0.106 |
| 2 | 2.1 kg | 0.64 | 0.077 |
| 3 | 5 kg | 0.24 | 0.028 |
| 4 | 50 g | 0.3 | 0.019 |
| 5 | 50 g | 0.2 | 0.016 |
| 6 | 50 g | 0.1 | 0.011 |
| 7 | 50 g | 0.1 | 0.011 |
| 8 | 1 kg | 0.01 | <0.01 |

Example 4

Pharmaceutical Composition Suitable for Injection or Intravenous Infusion and Determination of Particle Impurity An illustrative example of a suitable SNS-595 pharmaceutical composition comprises: 10 mg of substantially pure SNS-595 drug substance per mL of aqueous solution of 4.5% sorbitol that is adjusted to pH 2.5 with methanesulfonic acid. One protocol for making such a solution includes the following for making a 100 mg/10 mL presentation: 100 mg substantially pure SNS-595 substance (prepared following the methods described herein) and 450 mg D-sorbitol are added to distilled water; the volume is brought up to a volume of 10 mL; and the pH of the resulting solution is adjusted to 2.5 with methanesulfonic acid.

The resulting SNS-595 composition will be essentially free of visible particles and stable.

As noted, the presence of particulate matter can be determined using any convenient technique. For example, the presence of visible particles can be determined according to the method described by European Pharmacopeia 5.0, Section 2.9.20, the entirety of which is incorporated herein by reference. Specifically, an apparatus having a viewing station comprising (1) a matt black panel of appropriate size held in a vertical position; (2) a non-glare white panel of appropriate size held in a vertical position next to the black panel; and (3) an adjustable lampholder fitted with a suitable, shaded, white-light source and with a suitable light diffuser (e.g., a viewing illuminator containing two 13 W fluorescent tubes, each 525 mm in length) is used. The intensity of illumination at the viewing point is maintained between 2000 lux and 3750 lux. Adherent labels are removed from the container. The outside of the container is washed and dried on the outside. The container is gently swirled or inverted while ensuring that air bubbles are not introduced, and the container is observed for about 5 seconds in front of the white panel to determine the presence of visible particles. The container is then observed for about 5 seconds in front of the black panel to determine the presence of visible particles. If visible particles are detected, from viewing in front of either panel, the corresponding container is rejected.

Further, the light obscuration particle count test described in USP-NF General Chapter 788 may be used, which is incorporated herein by reference in its entirety. Specifically, a suitable apparatus based on the principle of light blockage which allows an automatic determination of the size of particles and the number of particles according to size is used. The apparatus is calibrated using dispersions of spherical particles of known sizes between 10 μm and 25 μm, USP Particle Count Reference Standard. These standard particles are dispersed in particle-free water. Care is taken to avoid aggregation of particles during dispersion.

The test is carried out under conditions limiting particulate matter, for example in a laminar-flow cabinet. The glassware and filtration equipment used is very carefully washed, except for the membrane filters, with a warm detergent solution and rinsed with abundant amounts of water to remove all traces of detergent. Immediately before use, the equipment is rinsed from top to bottom, outside and then inside, with particle-free water.

Care is taken not to introduce air bubbles into the preparation to be examined, especially when fractions of the preparation are being transferred to the container in which the determination is to be carried out. To check that the environment is suitable for the test, that the glassware is properly cleaned and that the water to be used is particle-free, the following test is carried out: determine the particulate matter in 5 samples of particle-free water, each of 5 mL, according to the method described below. If the number of particles of 10 μm or greater size exceeds 25 for the combined 25 mL, the precautions taken for the test are not sufficient. The preparatory steps are repeated until the environment, glassware and water are suitable for the test.

The contents of the sample are mixed by slowly inverting the container 20 times successively. If necessary, the sealing closure is cautiously removed. The outer surfaces of the container opening are cleaned using a jet of particle-free water and the closure is removed, avoiding any contamination of the contents. Gas bubbles are eliminated by appropriate measures such as allowing the sample to stand for 2 min or by sonication.

For small-volume parenteral products less than 25 mL in volume, the contents of 10 or more units are combined in a cleaned container to obtain a volume of not less than 25 mL; the test solution may be prepared by mixing the contents of a suitable number of vials and diluting to 25 mL with particle-free water or with an appropriate particle-free solvent when particle-free water is not suitable. Parenteral products having a volume of 25 mL or more may be tested individually.

The number of test specimens is such to afford a statistically sound assessment. For large-volume parenterals or for small-volume parenterals having a volume of 25 mL or more, fewer than 10 units may be tested, based on an appropriate sampling plan.

Four samples are removed from the specimen, each of not less than 5 mL, and the particles having diameters equal to or greater than each of 10 μm and 25 μm are counted. The result obtained for the first sample is disregarded, and the mean number of particles for the specimen is calculated.

Example 5

Synthesis of Compound 4

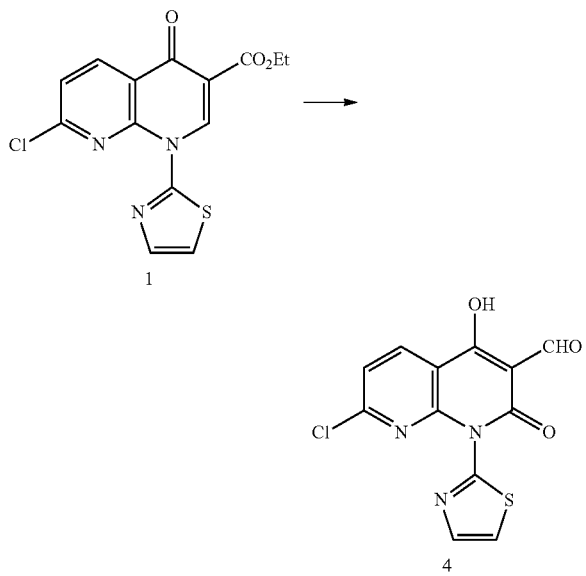

Compound 1 (100 g; 1.0 eq) was added to a solution of 25 g of LiOH—$H_2O$ (0.25 eq) in 625 mL water and 125 mL EtOH. The resulting slurry was mixed was stirred at 25-30° C. overnight. The reaction mixture was then filtered and washed with 500 mL water and 500 mL EtOH. The solids were then dried at 50° C. overnight in vacuo to afford Compound 4. $^1$H NMR (400 MHz, DMSO-$d_6$): δ 9.95 (s, 1H), 8.5 (d, J=8.4 Hz, 1H), 7.95 (d, J=4 Hz, 1H), 7.88 (d, J=3.2 Hz, 1H), 7.46 (d, J=8.8 Hz, 1H); $^{13}$C NMR (125 MHz, DMSO-$d_6$): 193.0, 171.2, 162.0, 155.6, 153.7, 152.0, 140.9, 137.9, 124.4, 119.9, 110.9, 106.4; MS: m/z 310, 308 (M+H)$^+$.

Example 6

Synthesis of Compound 6

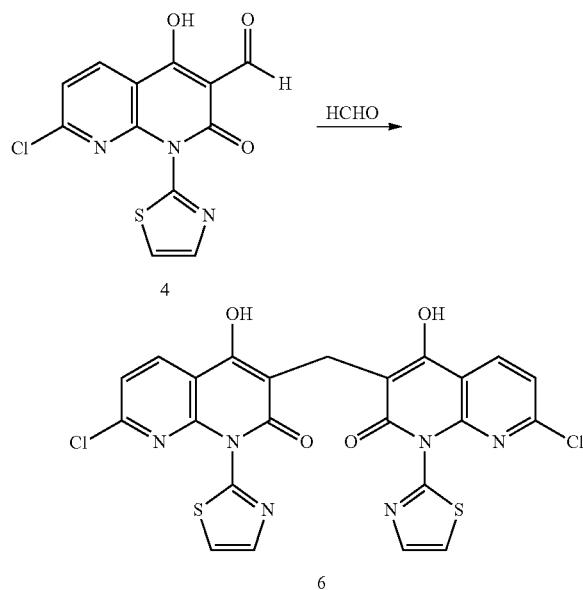

Compound 4 (10 g) was taken in 500 mL acetic acid. The resulting slurry was stirred for 15 minutes (min) at RT under nitrogen atmosphere. The slurry was then added to a 10 L 3-necked round bottom flask containing 4.5 L of 37% aqueous formaldehyde solution. The resulting slurry was then stirred at 60-62° C. overnight and cooled to 25-30° C. The reaction mixture was then filtered, and the resulting white powder was dried under vacuum at 25-30° C. overnight. The solid was re-suspended in 150 mL acetic acid and stirred for 3 days at RT. The resulting slurry was then filtered, and the solids were dried in a vacuum overnight to afford Compound 6. $^1$H NMR (400 MHz, DMSO-$d_6$): δ 8.38 (d, J=8.8 Hz, 2H), 7.97 (d, J=3.6 Hz, 2H), 7.89 (d, J=3.6 Hz, 2H), 7.46 (d, J=8 Hz, 2H), 3.89 (s, 2H); MS: m/z 571, 573, 575 (M+H)$^+$.

Compound 6 was analyzed by polarized light microscopy to assess its crystallinity and crystalline habit. Compound 6 appears to be a crystalline powder under polarized light microscope as it exhibits strong birefringence. The crystalline habit is that of plates 50-100 μm, as isolated from acetic acid.

Example 7

Preparation of Substantially Pure SNS-595 Substance from 2,6-Dichloronicotinic Acid and N-Boc-3-Pyrroline

Preparation of Compound 1 from 2,6-dichloronicotinic acid

A solution of carbonyldiimidazole (CDI) (16.4 kg) in tetrahydrofuran (THF) was added to a slurry of 2,6-dichloronicotinic acid (Compound A) (16 kg) in THF. After about 2 hr, ethyl potassium malonate (EtO$_2$CCH$_2$CO$_2$K) (19.4 kg), triethylamine (25.9 kg) and magnesium chloride (11.9 kg) were added and the reaction stirred for about 24 hr. The reaction mixture was quenched with dilute HCl and extracted with ethyl acetate. The organic layer was concentrated, washed with a mixture of aqueous NaCl and NaHCO$_3$. The organic layer was diluted with methylcyclohexane and dried by vacuum distillation. The solution was treated with triethylorthoformate (17.1 kg) and acetic anhydride (59 kg) at about 90 to 110° C. After the reaction was judged to be complete, the excess acetic anhydride was removed by distillations with methylcyclohexane. The crude product was treated with a solution of 2-aminothiazole (8.2 kg) in THF. After about 2 hr, the reaction mixture was treated with potassium carbonate (13.6 kg) and the mixture stirred for about 6 hr. The product was precipitated by the addition of water, isolated by filtration, washed with ACN-water, ACN, and dried to give Compound 1 (13.1 kg).

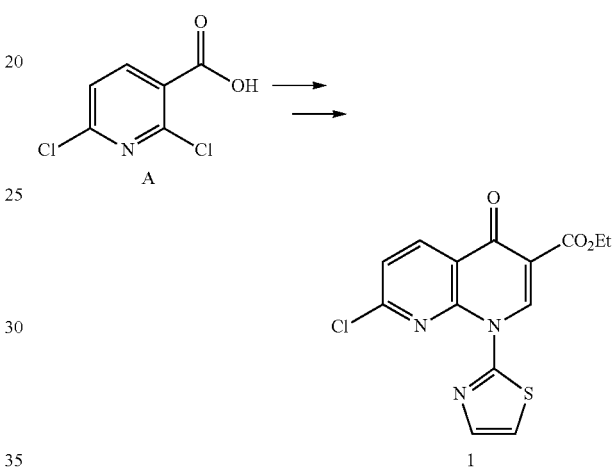

Preparation of Compound 2 N-Boc-3-pyrroline

(±)-3-Bromo-4-hydroxy-pyrrolidine-1-carboxylic acid, tert-butyl ester (2). (*Tetrahedron Asymmetry*, 12 (2002) 2989-2997)

N-Boc-3-pyrroline B (296 g, 1.75 moles) was added to a slurry of 1,3-dibromo-5,5-dimethylhydantoin (270 g, 0.94 moles) in acetonitrile (ACN, 1800 mL) and water (296 mL), while maintaining the temperature of the vessel at 0 to 10° C. After the addition, the reaction mixture was warmed to RT and stirred until the reaction was judged to be complete (TLC or HPLC). The reaction was quenched by the addition of 5% aqueous sodium thiosulfate solution (600 mL) and the product was extracted with dichloromethane (2×750 mL). The combined organic layer was washed with water (300 mL) and brine (200 mL). The organic layer was dried over anhydrous Na$_2$SO$_4$ (75 g) and concentrated under reduced pressure to give Compound B (450 g) which was directly used in the next step.

6-Oxa-3-aza-bicyclo[3.1.0]hexane-3-carboxylic acid, tert-butyl ester (Compound D)

An aqueous solution of sodium hydroxide (NaOH, 1.55 L, 2N) was added to Compound C (450 g, 1.69 moles) and the reaction was stirred between for 2 hr at about RT. The product was extracted with dichloromethane (2×1.25 L) and the combined organic layer was washed with water (2×750 mL) to neutral pH and then dried over anhydrous Na$_2$SO$_4$. Evaporation under reduced pressure gave the epoxide D (291.0 g).

(±)-3-Hydroxy-4-methylamino-pyrrolidine-1-carboxylic acid, tert-butyl ester (Compound E)

Aqueous methylamine solution (40% solution, 812 mL, 3.8 mol) was added to the epoxide D (140 g, 0.65 mol) at RT and the reaction was stirred until complete. The excess methylamine was removed by distillation under reduced pressure. To the residue obtained, diisopropyl ether (800 mL) was added and the mixture stirred for about 30 min. The solid was filtered, washed with diisopropyl ether (200 mL), then dried to give Compound E (135 g).

(±)-3-Hydroxy-4-methylamino-pyrrolidine-1-carboxylic acid, tert-butyl ester (Compound E), from Compound C.

Ten grams (10 g) of bromohydrin (Compound C) was treated with 40% aqueous methylamine (50 mL) and sodium bicarbonate (3.1 g) at RT to give Compound E (8.5 g).

Resolution of (±)-3-Hydroxy-4-methylamino-pyrrolidine-1-carboxylic acid, tert-butyl ester, using L-(−)-malic acid The aminoalcohol (Compound E) (100 g, 0.46 moles) was dissolved in a mixture of acetone (600 mL) and water (13 mL) at RT. The reaction mixture was heated to about 40° C. and L-(−)-malic acid (62 g, 0.48 moles) was added. The mixture was heated to about 50 to 55° C. to form a clear solution and then gradually cooled to RT and then to 5 to 10° C. The crystals formed were filtered, washed with acetone (2×70 mL), and dried under reduced pressure to give the malate salt F (60 g, 37%), with purity by chiral HPLC ratio of S to R enantiomers (S:R)=100:0.

A small sample was analyzed for enantiomeric purity by conversion to Compound G and analyzing the resulting Compound G by chiral HPLC (Chiracel OD-H SC522; mobile phase: hexane:IPA 95:5; 1 mL/min). The retention time for the S-enantiomer is 7.725 min.

Resolution of (±)-3-Hydroxy-4-methylamino-pyrrolidine-1-carboxylic acid, tert-butyl ester, using (L)-(−)-pyroglutamic acid Resolution of Compound E (10 g) with (L)-(−)-pyroglutamic acid (3.58 g) in acetone (120 mL) and water (4 mL) gave the pyroglutamate salt (5.7 g). Crystallization from acetone-water gave 4.2 g of the PGA salt with 94:6 ratio of diastereomers. An additional recrystallization from acetone-water gave the diastereomerically pure PGA salt (2.3 g, >99% de).

Preparation of 3-(tert-Butoxycarbonyl-methyl-amino)-4-hydroxy-pyrrolidine-1-carboxylic acid, tert-butyl ester (Compound G) from L-(−)-malic acid salt (Compound F)

To a mixture of Compound F (57 g, 0.16 moles) in methanol (MeOH, 220 mL), K$_2$CO$_3$ (68.0 g, 0.49 moles) was added at RT. Boc anhydride (40 g, 0.18 moles) was added dropwise to the reaction mixture over about 1 hr and the reaction mixture was stirred until the reaction was complete (about 2 hr). Methanol was distilled off under reduced pressure at about 55 to 60° C., water (150 mL) was added to the reaction mixture and the product was extracted with methyl tert-butyl ether (MTBE, 2×150 mL). The combined organic layer was washed with water (200 mL) and brine (100 mL), and then dried over anhydrous Na$_2$SO$_4$. Concentration under reduced pressure gave Compound G as a white solid (52 g).

3-(tert-Butoxycarbonyl-methyl-amino)-4-methoxy-pyrrolidine-1-carboxylic acid, tert-butyl ester (Compound H)

A suspension of Compound G (52 g, 0.16 mol) in THF (150 mL) was stirred at RT for about 30 min and cooled to −10 to −15° C. A solution of potassium hexamethyldisilylamide (KHMDS, 40 solution in THF, 144 mL, 0.256 mol) was slowly added while controlling the temperature between −5 and −15° C. After 15 min, dimethyl sulfate (18.7 mL, 1.20 mol) was added dropwise to the reaction mixture while maintaining a temperature between −10 and 0° C., and the resulting reaction mixture was then stirred at this temperature for about 30 min. The reaction mixture was quenched by the addition of water (100 mL), followed by acetic acid (50 mL). The product was extracted with methyl tert-butyl ether (2×150 mL). The combined organic layer was washed with water (100 mL), brine (50 mL) and dried over anhydrous Na$_2$SO$_4$. Evaporation under reduced pressure gave Compound H as an oil (54 g).

(+)-(4-Methoxy-pyrrolidin-3-yl)-methyl-amine (Compound 2), prepared using toluene-4-sulfonic acid (2:1)

To a solution of Compound H (54.0 g, 0.163 moles) in THF (180 mL) and MeOH (90 mL), p-toluene sulfonic acid monohydrate (84 g, 0.442 moles) was added and the reaction mixture was heated to 55-60° C. for about 5 hr, at which time the deprotection was complete. After cooling to about 40-45° C., 0.2 g seed crystals of Compound 2 was added to the reaction mixture resulting in immediate crystallization. The slurry was maintained at 40-45° C. for about 30 minutes and then gradually cooled to 0-5° C. After agitating for 2 hr at 0-5° C., solids were filtered, washed with THF (2×50 mL), and dried to give the tosylate salt Compound 2 as a white solid (66 g) with HPLC purity=98.9%.

The HPLC conditions were as follows: Column: Chiralcel AD-H, SC\523; mobile phase: Heptane: IPA (0.5% TFA) =85:15; flow rate: 1.0 mL/min, and runtime: 20 min.

Compound 2 has the retention time of 12.66 min. Enantiomeric excess of this material was greater than 99% ee.

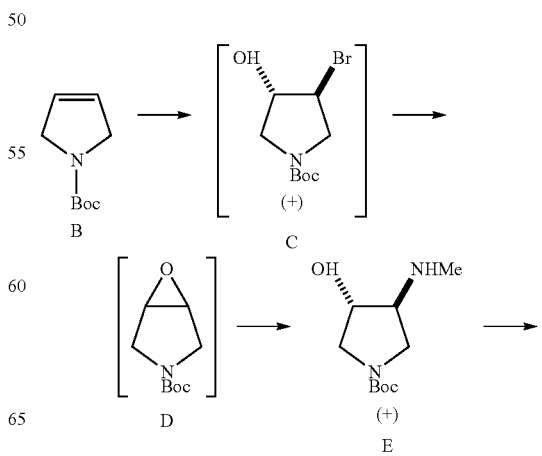

-continued

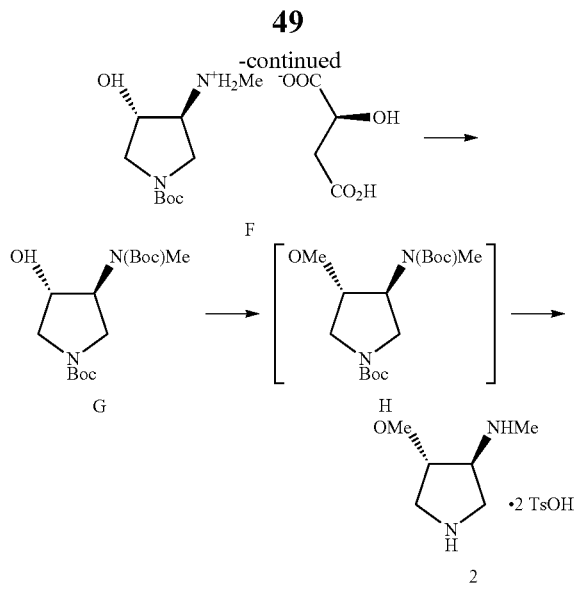

Preparation of Substantially Pure SNS-595 Substance Via Reprocessing.

To a slurry of Compound 2 (8.0 kg) in ACN at about 5° C., DIPEA (8.7 kg) is added. After about 15 min, Compound 1 (5.0 kg) is added to the reaction mixture. The reaction mixture is heated to about 45° C. for about 3 hr, cooled and the product filtered. The filter cake is washed with ACN and dried to give Compound 3.

To a solution of NaOH (0.8 kg) in water (19.5 kg), Compound 3 (5.5 kg) and EtOH (0.5 kg) are added. The reaction mixture is filtered and the filtrate acidified to pH 7.3-7.7 by the addition of acetic acid. The mixture is then heated to about 55-65° C. for about 2 hr. After cooling to ambient temperature, the reaction mixture is filtered and washed with water and then with EtOH. The filter cake is dried under vacuum. The crude product is slurried in EtOH at about 80° C. After cooling, the product is filtered, washed with EtOH and dried to give a SNS-595 mixture.

Next, to a solution of NaOH (0.2 kg) in water (4.8 kg), the SNS-595 mixture obtained above (1.49 kg) and EtOH (0.13 kg) are added. The reaction mixture is filtered and the filtrate acidified to pH 7.3-7.7 by the addition of aqueous acetic acid (prepared from 0.9 kg acetic acid and 2.9 kg water). The mixture is then heated to about 55-65° C. for about 2 hr. After cooling to ambient temperature, the reaction mixture is filtered and washed with water and then with EtOH. The filter cake is dried under vacuum. The crude product is slurried in EtOH at about 80° C. After cooling, the product is filtered, washed with EtOH and dried to give a substantially pure SNS-595 substance.

Preparation of Substantially Pure SNS-595 Substance Via Wet N,N-Diisopropylethylamine.

To a slurry of Compound 2 (1.55 kg) in acetonitrile (ACN; 10 L), diisopropylethylamine (DIPEA; 4 L) and water (0.5 L) were added. To the solution, Compound 1 (1 kg) and acetonitrile (1 L) were added and the reaction was stirred for about 12 hr at RT. The reaction mixture was then heated to about 45° C. for about 2-6 hr. After cooling, the product was filtered, washed with ACN (4 L) and dried under vacuum to give Compound 3 (1.1 kg). HPLC analysis showed this material to contain <0.1% Compound 1.

To a solution of NaOH (0.135 kg) in water (3.3 L), substantially pure Compound 3 (0.9 kg) and EtOH are added. After hydrolysis was complete, the reaction mixture was filtered and the filtrate acidified to pH 7.3-7.7 by the addition of aqueous acetic acid. The mixture was then heated to about 55-65° C. for about 2 hr. After cooling to ambient temperature, the reaction mixture was filtered and washed with water and then with EtOH. The filter cake is dried under vacuum. The crude product was slurried in EtOH at about 80° C. After cooling, the product was filtered, washed with EtOH, and dried to give a substantially pure SNS-595 substance (0.66 kg).

The embodiments of the claimed subject matter described above are intended to be merely exemplary, and those skilled in the art will recognize, or will be able to ascertain using no more than routine experimentation, numerous equivalents of specific compounds, materials, and procedures. All such equivalents are considered to be within the scope of the claimed subject matter and are encompassed by the appended claims.

What is claimed:

1. A process for preparing a substantially pure SNS-595 substance, comprising:
   (a) reacting Compound 3

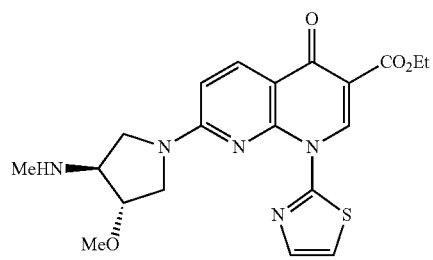

with a first aqueous base followed by neutralizing to obtain a primary SNS-595 hydrate;
   (b) dehydrating the primary SNS-595 hydrate from step (a) and reacting the dehydrated product with a second aqueous base followed by neutralizing to obtain a secondary SNS-595 hydrate; and
   (c) dehydrating the secondary SNS-595 hydrate obtained in step (b) to obtain the substantially pure SNS-595 substance.

2. The process of claim 1, wherein the first and second aqueous bases are selected from potassium hydroxide, sodium hydroxide, and lithium hydroxide; the neutralizations of steps (a) and (b) are accomplished with acetic acid; and the dehydration of steps (b) and (c) are accomplished with ethanol.

3. The process of claim 2, wherein the substantially pure SNS-595 substance obtained from step (c) comprises about 0 to 0.01% Compound 4

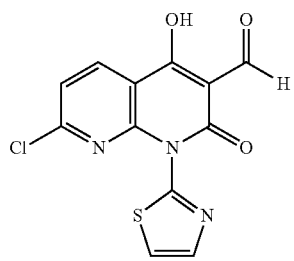

based on total weight of the substantially pure SNS-595 substance.

4. The process of claim 1, wherein Compound 3 is obtained by reaction of Compound 1

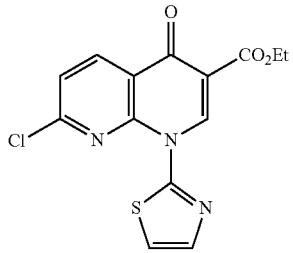

with Compound 2

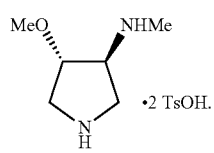

5. A process for preparing substantially pure Compound 3

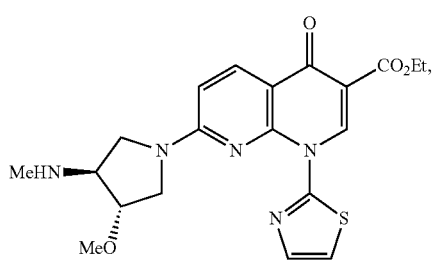

comprising reacting Compound 1

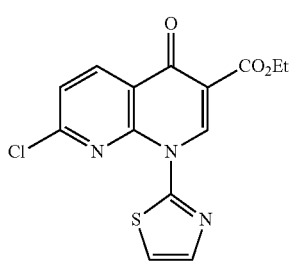

with Compound 2

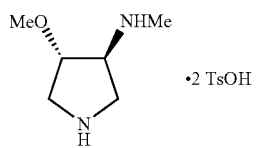

in the presence of N,N-diisopropylethylamine and water to obtain substantially pure Compound 3.

6. The process of claim 5, wherein the substantially pure Compound 3 obtained comprises from 0 to about 0.1% Compound 1

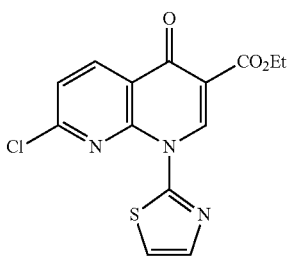

based on total weight of substantially pure Compound 3.

7. A process for preparing a substantially pure SNS-595 substance, comprising:
(a) reacting Compound 1

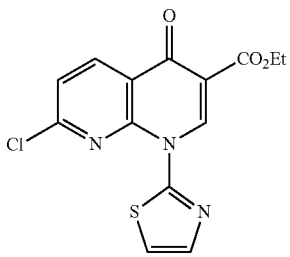

with Compound 2

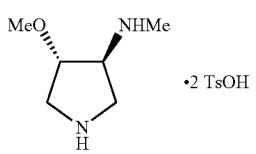

in the presence of N,N-diisopropylethylamine and water to obtain substantially pure Compound 3

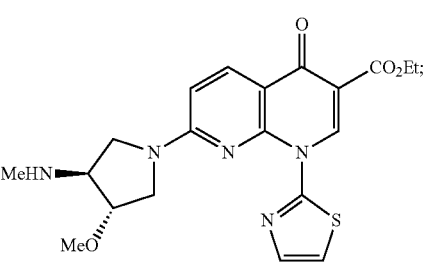

(b) reacting the substantially pure Compound 3 with an aqueous base followed by neutralizing to obtain a primary SNS-595 hydrate; and
(c) dehydrating the primary SNS-595 hydrate obtained in step (a) to obtain the substantially pure SNS-595 substance.

8. The process of claim 7, wherein the substantially pure Compound 3 obtained comprises about 0 to 0.1% Compound 1

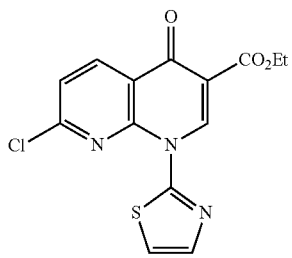

based on total weight of the substantially pure Compound 3.

9. The process of claim 7, wherein the substantially pure SNS-595 substance obtained from step (c) comprises about 0 to 0.01% Compound 4

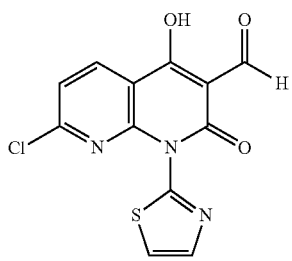

based on total weight of the substantially pure SNS-595 substance.

10. The process of claim 7, wherein the substantially pure SNS-595 substance obtained from step (b) comprises about 0 to 0.02% Compound 5

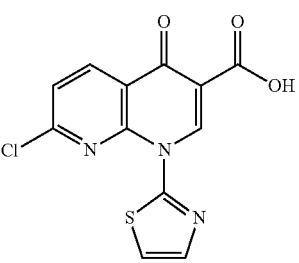

based on total weight of the substantially pure SNS-595 substance.

11. The process of claim 2, wherein the first and second aqueous bases are sodium hydroxide.

12. The process claim 1, wherein the SNS-595 substance obtained from step (c) comprises 0 to 0.02% Compound 5:

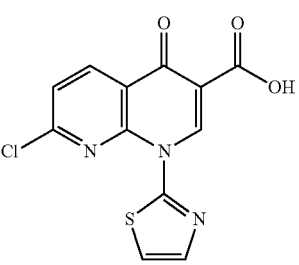

based on total weight of the SNS-595 substance.

13. The process of claim 1, wherein the SNS-595 substance obtained from step (c) comprises 0 to 0.1% Compound 7:

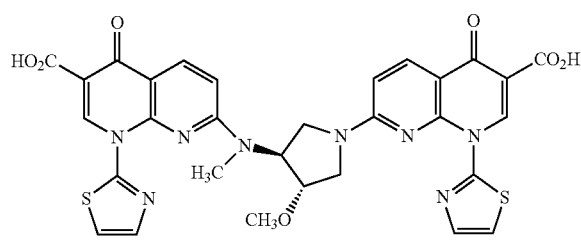

based on total weight of the SNS-595 substance.

14. The process of claim 1, wherein Compound 3 is obtained by reaction of Compound 1

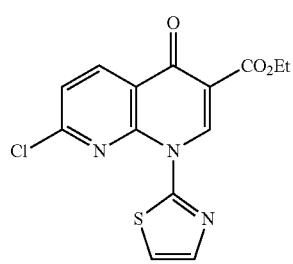

with Compound 2

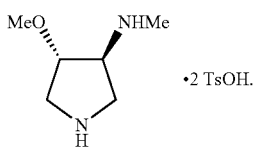

15. The process of claim 1, comprising:
(a) reacting Compound 1

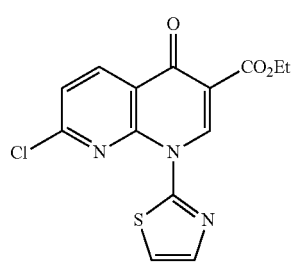

with Compound 2

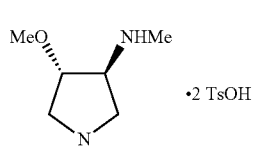

in the presence of DIPEA and water to obtain Compound 3

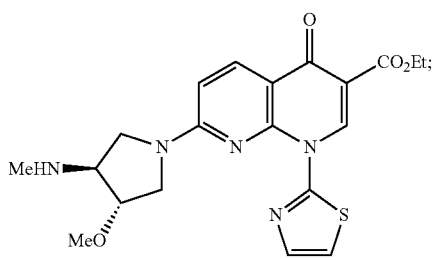

(b) reacting Compound 3 with a first aqueous base followed by neutralizing to obtain a primary SNS-595 hydrate;
(c) dehydrating the primary SNS-595 hydrate obtained in step (b) to form a SNS-595 substance;
(d) reacting the SNS-595 substance from step (c) with a second aqueous base followed by neutralizing to obtain a secondary SNS-595 hydrate; and
(e) dehydrating the secondary SNS-595 hydrate obtained in step (d) to obtain SNS-595 substance.

16. The process claim 1, wherein the SNS-595 substance obtained from step (c) comprises
about 0 to 0.02% Compound 4

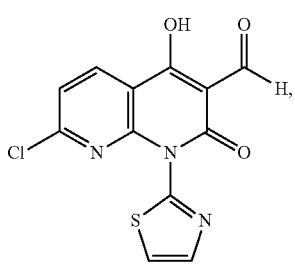

about 0 to 0.02% Compound 5:

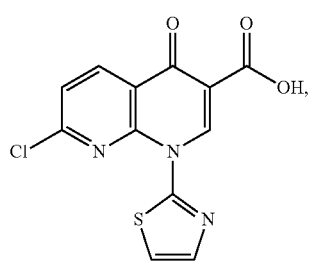

and about 0 to 0.1% Compound 7:

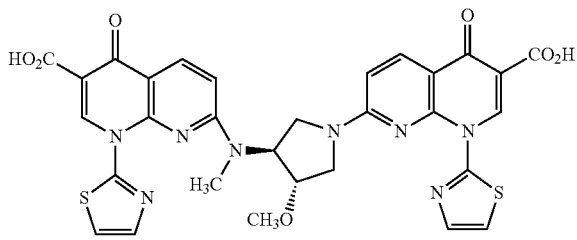

based on total weight of the SNS-595 substance.

* * * * *